(12) United States Patent
Winslow et al.

(10) Patent No.: US 8,430,916 B1
(45) Date of Patent: Apr. 30, 2013

(54) SPINAL ROD CONNECTORS, METHODS OF USE, AND SPINAL PROSTHESIS INCORPORATING SPINAL ROD CONNECTORS

(75) Inventors: Charles J. Winslow, Lafayette, CA (US); Steven T. Mitchell, Pleasant Hill, CA (US)

(73) Assignee: Spartek Medical, Inc., Concord, CA (US)

( * ) Notice: Subject to any disclaimer, the term of this patent is extended or adjusted under 35 U.S.C. 154(b) by 0 days.

(21) Appl. No.: 13/368,166

(22) Filed: Feb. 7, 2012

(51) Int. Cl.
*A61B 17/70* (2006.01)

(52) U.S. Cl.
USPC ........................................... 606/278; 606/250

(58) Field of Classification Search .................. 606/246, 606/250–253, 260, 278
See application file for complete search history.

(56) References Cited

U.S. PATENT DOCUMENTS

| | | |
|---|---|---|
| 4,041,939 A | 8/1977 | Hall |
| 4,065,817 A | 1/1978 | Branemark et al. |
| 4,274,401 A | 6/1981 | Miskew |
| 4,347,845 A | 9/1982 | Mayfield |
| 4,369,770 A | 1/1983 | Bacal et al. |
| 4,382,438 A | 5/1983 | Jacobs |
| 4,409,968 A | 10/1983 | Drummond |
| 4,411,259 A | 10/1983 | Drummond |
| 4,422,451 A | 12/1983 | Kalamchi |
| 4,479,491 A | 10/1984 | Martin |
| 4,567,885 A | 2/1986 | Androphy |
| 4,573,454 A | 3/1986 | Hoffman |
| 4,604,995 A | 8/1986 | Stephens et al. |
| 4,611,580 A | 9/1986 | Wu |
| 4,611,581 A | 9/1986 | Steffee |
| 4,611,582 A | 9/1986 | Duff |
| 4,641,636 A | 2/1987 | Cotrel |
| 4,648,388 A | 3/1987 | Steffee |
| 4,653,481 A | 3/1987 | Howland et al. |
| 4,653,489 A | 3/1987 | Tronzo |
| 4,655,199 A | 4/1987 | Steffee |
| 4,658,809 A | 4/1987 | Ulrich et al. |
| 4,696,290 A | 9/1987 | Steffee |
| 4,719,905 A | 1/1988 | Steffee |

(Continued)

FOREIGN PATENT DOCUMENTS

| | | |
|---|---|---|
| DE | 2649042 B1 | 10/1976 |
| DE | 3639810 A1 | 5/1988 |

(Continued)

OTHER PUBLICATIONS

International Search Report for PCT/US2011/057403 dated May 8, 2012, 17 pages.

(Continued)

*Primary Examiner* — Eduardo C Robert
*Assistant Examiner* — Christina Negrellirodriguez
(74) *Attorney, Agent, or Firm* — Fliesler Meyer LLP

(57) ABSTRACT

A spinal rod connector is adapted to connect two spinal rods. The spinal rod connector includes first and second channels which are defined in a housing. The first and second channels can be urged together in order to capture first and second spinal rods when a fastener is actuated. The spinal rod connector allows the first and second rods to be positioned relative to each other in one of a parallel and a non-parallel manner prior to the fastener locking the first and second spinal rods in position.

9 Claims, 16 Drawing Sheets

U.S. PATENT DOCUMENTS

| | | |
|---|---|---|
| 4,763,644 A | 8/1988 | Webb |
| 4,773,402 A | 9/1988 | Asher et al. |
| 4,805,602 A | 2/1989 | Puno et al. |
| 4,815,453 A | 3/1989 | Cotrel |
| 4,887,595 A | 12/1989 | Heinig et al. |
| 4,913,134 A | 4/1990 | Luque |
| 4,946,458 A | 8/1990 | Harms et al. |
| 4,950,269 A | 8/1990 | Gaines, Jr. |
| 4,955,885 A | 9/1990 | Meyers |
| 4,987,892 A | 1/1991 | Krag et al. |
| 5,005,562 A | 4/1991 | Cotrel |
| 5,024,213 A | 6/1991 | Asher et al. |
| 5,030,220 A | 7/1991 | Howland |
| 5,042,982 A | 8/1991 | Harms et al. |
| 5,047,029 A | 9/1991 | Aebi et al. |
| 5,067,955 A | 11/1991 | Cotrel |
| 5,074,864 A | 12/1991 | Cozad et al. |
| 5,084,049 A | 1/1992 | Asher et al. |
| 5,092,866 A | 3/1992 | Breard et al. |
| 5,102,412 A | 4/1992 | Rogozinski |
| 5,112,332 A | 5/1992 | Cozad et al. |
| 5,113,685 A | 5/1992 | Asher et al. |
| 5,116,334 A | 5/1992 | Cozad et al. |
| 5,127,912 A | 7/1992 | Ray et al. |
| 5,129,388 A | 7/1992 | Vignaud et al. |
| 5,129,900 A | 7/1992 | Asher et al. |
| 5,147,359 A | 9/1992 | Cozad et al. |
| 5,154,718 A | 10/1992 | Cozad et al. |
| 5,176,680 A | 1/1993 | Vignaud et al. |
| 5,180,393 A | 1/1993 | Commarmond |
| 5,190,543 A | 3/1993 | Schläpfer |
| 5,201,734 A | 4/1993 | Cozad et al. |
| 5,207,678 A | 5/1993 | Harms et al. |
| 5,258,031 A | 11/1993 | Salib et al. |
| 5,261,911 A | 11/1993 | Carl |
| 5,261,912 A | 11/1993 | Frigg |
| 5,261,913 A | 11/1993 | Marnay |
| 5,281,222 A | 1/1994 | Allard et al. |
| 5,282,801 A | 2/1994 | Sherman |
| 5,282,863 A | 2/1994 | Burton |
| 5,290,289 A | 3/1994 | Sanders et al. |
| 5,312,402 A | 5/1994 | Schläpfer et al. |
| 5,312,404 A | 5/1994 | Asher et al. |
| 5,344,422 A | 9/1994 | Frigg |
| 5,346,493 A | 9/1994 | Stahurski et al. |
| 5,360,429 A | 11/1994 | Jeanson et al. |
| 5,360,431 A | 11/1994 | Puno et al. |
| 5,374,267 A | 12/1994 | Siegal |
| 5,380,325 A | 1/1995 | Lahille et al. |
| 5,380,326 A | 1/1995 | Lin |
| 5,382,248 A | 1/1995 | Jacobson et al. |
| 5,385,583 A | 1/1995 | Cotrel |
| 5,387,213 A | 2/1995 | Breard et al. |
| 5,415,661 A | 5/1995 | Holmes |
| 5,429,639 A | 7/1995 | Judet |
| 5,437,672 A | 8/1995 | Alleyne |
| 5,443,467 A | 8/1995 | Biedermann et al. |
| 5,466,237 A | 11/1995 | Byrd, III et al. |
| 5,474,555 A | 12/1995 | Puno et al. |
| 5,480,442 A | 1/1996 | Bertanoli |
| 5,487,742 A | 1/1996 | Cotrel |
| 5,496,321 A | 3/1996 | Puno et al. |
| 5,498,264 A | 3/1996 | Schlapfer et al. |
| 5,501,684 A | 3/1996 | Schlapfer et al. |
| 5,520,689 A | 5/1996 | Schläpfer et al. |
| 5,534,001 A | 7/1996 | Schlapfer et al. |
| 5,536,268 A | 7/1996 | Griss |
| 5,540,688 A | 7/1996 | Navas |
| 5,545,167 A | 8/1996 | Lin |
| 5,549,607 A | 8/1996 | Olson et al. |
| 5,562,737 A | 10/1996 | Graf |
| 5,569,248 A | 10/1996 | Mathews |
| 5,591,166 A | 1/1997 | Bernhardt et al. |
| 5,601,552 A | 2/1997 | Cotrel |
| 5,609,592 A | 3/1997 | Brumfield et al. |
| 5,609,593 A | 3/1997 | Errico et al. |
| 5,611,800 A | 3/1997 | Davis et al. |
| 5,624,441 A | 4/1997 | Sherman et al. |
| 5,628,740 A | 5/1997 | Mullane |
| 5,630,816 A | 5/1997 | Kambin |
| 5,643,260 A | 7/1997 | Doherty |
| 5,645,599 A | 7/1997 | Samani |
| 5,651,789 A | 7/1997 | Cotrel |
| 5,653,708 A | 8/1997 | Howland |
| 5,658,284 A | 8/1997 | Sebastian et al. |
| 5,658,285 A | 8/1997 | Marnay et al. |
| 5,667,506 A | 9/1997 | Sutterlin |
| 5,667,507 A | 9/1997 | Corin et al. |
| 5,669,910 A | 9/1997 | Korhonen et al. |
| 5,672,175 A | 9/1997 | Martin |
| 5,672,176 A | 9/1997 | Biedermann et al. |
| 5,676,665 A | 10/1997 | Bryan |
| 5,676,703 A | 10/1997 | Gelbard |
| 5,681,310 A | 10/1997 | Yuan et al. |
| 5,681,311 A | 10/1997 | Foley et al. |
| 5,681,319 A | 10/1997 | Biedermann et al. |
| 5,683,391 A | 11/1997 | Boyd |
| 5,683,392 A | 11/1997 | Richelsoph et al. |
| 5,683,393 A | 11/1997 | Ralph |
| 5,688,272 A | 11/1997 | Montague et al. |
| 5,688,273 A | 11/1997 | Errico et al. |
| 5,690,629 A | 11/1997 | Asher et al. |
| 5,690,632 A | 11/1997 | Schwartz et al. |
| 5,690,633 A | 11/1997 | Taylor et al. |
| 5,693,053 A | 12/1997 | Estes |
| 5,697,929 A | 12/1997 | Mellinger |
| 5,700,292 A | 12/1997 | Margulies |
| 5,702,392 A | 12/1997 | Wu et al. |
| 5,702,394 A | 12/1997 | Henry et al. |
| 5,702,395 A | 12/1997 | Hopf |
| 5,702,396 A | 12/1997 | Hoenig et al. |
| 5,702,399 A | 12/1997 | Kilpela et al. |
| 5,702,452 A | 12/1997 | Argenson et al. |
| 5,713,900 A | 2/1998 | Benzel et al. |
| 5,713,904 A | 2/1998 | Errico et al. |
| 5,716,355 A | 2/1998 | Jackson et al. |
| 5,716,356 A | 2/1998 | Biedermann et al. |
| 5,716,357 A | 2/1998 | Rogozinski |
| 5,716,358 A | 2/1998 | Ochoa et al. |
| 5,716,359 A | 2/1998 | Ojima et al. |
| 5,720,751 A | 2/1998 | Jackson |
| 5,725,528 A | 3/1998 | Errico et al. |
| 5,725,582 A | 3/1998 | Bevan et al. |
| 5,728,098 A | 3/1998 | Sherman et al. |
| 5,733,286 A | 3/1998 | Errico et al. |
| 5,735,851 A | 4/1998 | Errico et al. |
| 5,741,254 A | 4/1998 | Henry et al. |
| 5,743,907 A | 4/1998 | Asher et al. |
| 5,743,911 A | 4/1998 | Cotrel |
| 5,752,957 A | 5/1998 | Ralph et al. |
| 5,766,254 A | 6/1998 | Gelbard |
| 5,776,135 A | 7/1998 | Errico et al. |
| 5,782,833 A | 7/1998 | Haider |
| 5,785,711 A | 7/1998 | Errico et al. |
| 5,797,911 A | 8/1998 | Sherman et al. |
| 5,800,435 A | 9/1998 | Errico et al. |
| 5,810,819 A | 9/1998 | Errico et al. |
| 5,863,293 A | 1/1999 | Richelsoph |
| 5,868,745 A | 2/1999 | Alleyne |
| 5,879,350 A | 3/1999 | Sherman et al. |
| 5,885,286 A | 3/1999 | Sherman et al. |
| 5,891,145 A | 4/1999 | Morrison et al. |
| 5,899,904 A | 5/1999 | Errico et al. |
| RE36,221 E | 6/1999 | Breard et al. |
| 5,910,142 A | 6/1999 | Tatar |
| 5,925,047 A | 7/1999 | Errico et al. |
| 5,928,231 A | 7/1999 | Klein et al. |
| 5,928,232 A | 7/1999 | Howland et al. |
| 5,928,233 A | 7/1999 | Apfelbaum et al. |
| 5,947,965 A | 9/1999 | Bryan |
| 5,947,969 A | 9/1999 | Errico et al. |
| 5,954,725 A | 9/1999 | Sherman et al. |
| 5,961,517 A | 10/1999 | Biedermann et al. |
| 5,964,760 A | 10/1999 | Richelsoph |
| 5,980,521 A | 11/1999 | Montague et al. |
| 5,980,523 A | 11/1999 | Jackson |
| 5,984,922 A | 11/1999 | McKay |

| Patent No. | Date | Inventor |
|---|---|---|
| 5,989,251 A | 11/1999 | Nichols |
| 5,989,254 A | 11/1999 | Katz |
| 6,001,098 A | 12/1999 | Metz-Stavenhagen et al. |
| 6,004,322 A | 12/1999 | Bernstein |
| 6,010,503 A | 1/2000 | Richelsoph et al. |
| 6,015,409 A | 1/2000 | Jackson |
| 6,033,410 A | 3/2000 | McLean et al. |
| 6,036,693 A | 3/2000 | Yuan et al. |
| 6,050,997 A | 4/2000 | Mullane |
| 6,053,917 A | 4/2000 | Sherman et al. |
| 6,063,089 A | 5/2000 | Errico et al. |
| 6,077,262 A | 6/2000 | Schläpfer et al. |
| 6,086,588 A | 7/2000 | Ameil et al. |
| 6,090,111 A | 7/2000 | Nichols |
| 6,096,039 A | 8/2000 | Stoltenberg et al. |
| 6,113,600 A | 9/2000 | Drummond et al. |
| 6,113,601 A | 9/2000 | Tatar |
| 6,123,706 A | 9/2000 | Lange |
| 6,127,597 A | 10/2000 | Beyar et al. |
| 6,132,430 A | 10/2000 | Wagner |
| 6,132,434 A | 10/2000 | Sherman et al. |
| 6,132,464 A | 10/2000 | Martin |
| 6,136,000 A | 10/2000 | Louis et al. |
| 6,146,383 A | 11/2000 | Studer et al. |
| 6,171,311 B1 | 1/2001 | Richelsoph |
| 6,193,720 B1 | 2/2001 | Yuan et al. |
| 6,197,028 B1 | 3/2001 | Ray et al. |
| 6,210,413 B1 | 4/2001 | Justis et al. |
| 6,217,578 B1 | 4/2001 | Crozet et al. |
| 6,248,106 B1 | 6/2001 | Ferree |
| 6,254,602 B1 | 7/2001 | Justis |
| 6,261,287 B1 | 7/2001 | Metz-Stavenhagen |
| 6,267,765 B1 | 7/2001 | Taylor et al. |
| 6,273,888 B1 | 8/2001 | Justis |
| 6,273,914 B1 | 8/2001 | Papas |
| 6,280,442 B1 | 8/2001 | Barker et al. |
| 6,280,443 B1 | 8/2001 | Gu et al. |
| 6,287,311 B1 | 9/2001 | Sherman et al. |
| 6,293,949 B1 | 9/2001 | Justis et al. |
| 6,302,882 B1 | 10/2001 | Lin et al. |
| 6,302,888 B1 | 10/2001 | Mellinger et al. |
| 6,309,391 B1 | 10/2001 | Crandall et al. |
| 6,325,802 B1 | 12/2001 | Frigg |
| 6,328,740 B1 | 12/2001 | Richelsoph |
| 6,344,057 B1 | 2/2002 | Rabbe et al. |
| 6,355,040 B1 | 3/2002 | Richelsoph et al. |
| 6,379,354 B1 | 4/2002 | Rogozinski |
| 6,402,749 B1 | 6/2002 | Ashman |
| 6,402,751 B1 | 6/2002 | Hoeck et al. |
| 6,402,752 B2 | 6/2002 | Schäffler-Wachter et al. |
| 6,413,257 B1 | 7/2002 | Lin et al. |
| 6,416,515 B1 | 7/2002 | Wagner |
| 6,423,064 B1 | 7/2002 | Kluger |
| 6,440,169 B1 | 8/2002 | Elberg et al. |
| 6,451,021 B1 | 9/2002 | Ralph et al. |
| 6,454,773 B1 | 9/2002 | Sherman et al. |
| 6,458,131 B1 | 10/2002 | Ray |
| 6,458,132 B2 | 10/2002 | Choi |
| 6,468,276 B1 | 10/2002 | McKay |
| 6,471,705 B1 | 10/2002 | Biedermann et al. |
| 6,475,219 B1 | 11/2002 | Shelokov |
| 6,478,797 B1 | 11/2002 | Paul |
| 6,482,207 B1 | 11/2002 | Errico |
| 6,485,491 B1 | 11/2002 | Farris et al. |
| 6,488,681 B2 | 12/2002 | Martin et al. |
| 6,520,962 B1 | 2/2003 | Taylor et al. |
| 6,520,990 B1 | 2/2003 | Ray |
| 6,537,276 B2 | 3/2003 | Metz-Stavenhagen |
| 6,540,748 B2 | 4/2003 | Lombardo |
| 6,540,749 B2 | 4/2003 | Schäfer et al. |
| 6,547,789 B1 | 4/2003 | Ventre et al. |
| 6,554,831 B1 | 4/2003 | Rivard et al. |
| 6,554,832 B2 | 4/2003 | Shluzas |
| 6,554,834 B1 | 4/2003 | Crozet et al. |
| 6,565,565 B1 | 5/2003 | Yuan et al. |
| 6,565,566 B1 | 5/2003 | Wagner et al. |
| 6,565,567 B1 | 5/2003 | Haider |
| 6,565,605 B2 | 5/2003 | Goble et al. |
| 6,572,617 B1 | 6/2003 | Senegas |
| 6,572,653 B1 | 6/2003 | Simonson |
| 6,579,290 B1 | 6/2003 | Hardcastle et al. |
| 6,585,737 B1 | 7/2003 | Baccelli et al. |
| 6,589,243 B1 | 7/2003 | Viart et al. |
| 6,616,669 B2 | 9/2003 | Ogilvie et al. |
| 6,623,485 B2 | 9/2003 | Doubler et al. |
| 6,626,905 B1 | 9/2003 | Schmiel et al. |
| 6,626,908 B2 | 9/2003 | Cooper et al. |
| 6,645,207 B2 | 11/2003 | Dixon et al. |
| 6,652,526 B1 | 11/2003 | Arafiles |
| 6,656,181 B2 | 12/2003 | Dixon et al. |
| 6,660,004 B2 | 12/2003 | Barker et al. |
| 6,660,005 B2 | 12/2003 | Toyama et al. |
| 6,676,661 B1 | 1/2004 | Martin Benlloch et al. |
| 6,695,845 B2 | 2/2004 | Dixon et al. |
| 6,706,045 B2 | 3/2004 | Lin et al. |
| 6,709,434 B1 | 3/2004 | Gournay et al. |
| 6,716,213 B2 | 4/2004 | Shitoto |
| 6,716,214 B1 | 4/2004 | Jackson |
| 6,726,689 B2 | 4/2004 | Jackson |
| 6,736,820 B2 | 5/2004 | Biedermann et al. |
| 6,740,086 B2 | 5/2004 | Richelsoph |
| 6,749,614 B2 | 6/2004 | Teitelbaum et al. |
| 6,752,807 B2 | 6/2004 | Lin et al. |
| 6,755,829 B1 | 6/2004 | Bono et al. |
| 6,755,835 B2 | 6/2004 | Schultheiss et al. |
| 6,761,719 B2 | 7/2004 | Justis et al. |
| 6,783,526 B1 | 8/2004 | Lin et al. |
| 6,783,527 B2 | 8/2004 | Drewry et al. |
| 6,786,907 B2 | 9/2004 | Lange |
| 6,793,656 B1 | 9/2004 | Mathews |
| 6,805,695 B2 | 10/2004 | Keith et al. |
| 6,805,714 B2 | 10/2004 | Sutcliffe |
| 6,811,567 B2 | 11/2004 | Reiley |
| 6,827,743 B2 | 12/2004 | Eisermann et al. |
| 6,832,999 B2 | 12/2004 | Ueyama et al. |
| 6,840,940 B2 | 1/2005 | Ralph et al. |
| 6,843,791 B2 | 1/2005 | Serhan |
| 6,852,128 B2 | 2/2005 | Lange |
| 6,858,029 B2 | 2/2005 | Yeh |
| 6,858,030 B2 | 2/2005 | Martin et al. |
| 6,869,433 B2 | 3/2005 | Glascott |
| 6,875,211 B2 | 4/2005 | Nichols et al. |
| 6,881,215 B2 | 4/2005 | Assaker et al. |
| 6,883,520 B2 | 4/2005 | Lambrecht et al. |
| 6,887,242 B2 | 5/2005 | Doubler et al. |
| 6,899,714 B2 | 5/2005 | Vaughan |
| 6,918,911 B2 | 7/2005 | Biedermann et al. |
| 6,932,817 B2 | 8/2005 | Baynham et al. |
| 6,945,974 B2 | 9/2005 | Dalton |
| 6,951,561 B2 | 10/2005 | Warren et al. |
| 6,964,666 B2 | 11/2005 | Jackson |
| 6,966,910 B2 | 11/2005 | Ritland |
| 6,986,771 B2 | 1/2006 | Paul et al. |
| 6,991,632 B2 | 1/2006 | Ritland |
| 7,008,423 B2 | 3/2006 | Assaker et al. |
| 7,011,685 B2 | 3/2006 | Arnin et al. |
| 7,018,378 B2 | 3/2006 | Biedermann et al. |
| 7,018,379 B2 | 3/2006 | Drewry |
| 7,022,122 B2 | 4/2006 | Amrein et al. |
| 7,029,475 B2 | 4/2006 | Panjabi |
| 7,033,392 B2 | 4/2006 | Schmiel et al. |
| 7,048,736 B2 | 5/2006 | Robinson et al. |
| 7,051,451 B2 | 5/2006 | Augostino et al. |
| 7,060,066 B2 | 6/2006 | Zhao et al. |
| 7,066,938 B2 | 6/2006 | Slivka et al. |
| 7,074,237 B2 | 7/2006 | Goble et al. |
| 7,081,117 B2 | 7/2006 | Bono et al. |
| 7,083,621 B2 | 8/2006 | Shaolian et al. |
| 7,083,622 B2 | 8/2006 | Simonson |
| 7,087,056 B2 | 8/2006 | Vaughan |
| 7,087,057 B2 | 8/2006 | Konieczynski et al. |
| 7,087,084 B2 | 8/2006 | Reiley |
| 7,090,698 B2 | 8/2006 | Goble et al. |
| 7,101,398 B2 | 9/2006 | Dooris et al. |
| 7,104,991 B2 | 9/2006 | Dixon et al. |
| 7,104,992 B2 | 9/2006 | Bailey |
| 7,107,091 B2 | 9/2006 | Jutras et al. |
| 7,125,410 B2 | 10/2006 | Freudiger |

| Patent No. | Date | Inventor |
|---|---|---|
| 7,125,426 B2 | 10/2006 | Moumene et al. |
| 7,137,985 B2 | 11/2006 | Jahng |
| 7,163,538 B2 | 1/2007 | Altarac et al. |
| 7,189,235 B2 | 3/2007 | Cauthen |
| 7,214,227 B2 | 5/2007 | Colleran et al. |
| 7,250,052 B2 | 7/2007 | Landry et al. |
| 7,270,665 B2 | 9/2007 | Morrison et al. |
| 7,282,064 B2 | 10/2007 | Chin |
| 7,294,128 B2 | 11/2007 | Alleyne et al. |
| 7,294,129 B2 | 11/2007 | Hawkins et al. |
| 7,306,603 B2 | 12/2007 | Boehm, Jr. et al. |
| 7,306,606 B2 | 12/2007 | Sasing |
| 7,309,355 B2 | 12/2007 | Donnelly et al. |
| 7,326,210 B2 | 2/2008 | Jahng et al. |
| 7,335,201 B2 | 2/2008 | Doubler et al. |
| 7,338,490 B2 | 3/2008 | Ogilvie et al. |
| 7,338,491 B2 | 3/2008 | Baker et al. |
| 7,344,539 B2 | 3/2008 | Serhan et al. |
| 7,361,196 B2 | 4/2008 | Fallin et al. |
| 7,371,238 B2 | 5/2008 | Soboleski et al. |
| 7,377,923 B2 | 5/2008 | Purcell et al. |
| 7,445,627 B2 | 11/2008 | Hawkes et al. |
| 7,455,684 B2 | 11/2008 | Gradel et al. |
| 7,476,238 B2 | 1/2009 | Panjabi |
| 7,479,156 B2 | 1/2009 | Lourdel et al. |
| 7,481,828 B2 | 1/2009 | Mazda et al. |
| 7,491,218 B2 | 2/2009 | Landry et al. |
| 7,503,924 B2 | 3/2009 | Lee et al. |
| 7,513,905 B2 | 4/2009 | Jackson |
| 7,513,911 B2 | 4/2009 | Lambrecht et al. |
| 7,520,879 B2 | 4/2009 | Justis |
| 7,530,992 B2 | 5/2009 | Biedermann et al. |
| 7,533,672 B2 | 5/2009 | Morgan et al. |
| 7,553,320 B2 | 6/2009 | Molz, IV et al. |
| 7,553,329 B2 | 6/2009 | Lambrecht et al. |
| 7,559,943 B2 | 7/2009 | Mujwid |
| 7,563,274 B2 | 7/2009 | Justis et al. |
| 7,572,279 B2 | 8/2009 | Jackson |
| 7,578,833 B2 | 8/2009 | Bray |
| 7,585,312 B2 | 9/2009 | Rawlins et al. |
| 7,588,575 B2 | 9/2009 | Colleran et al. |
| 7,588,588 B2 | 9/2009 | Spitler et al. |
| 7,594,924 B2 | 9/2009 | Albert et al. |
| 7,597,707 B2 | 10/2009 | Freudiger |
| 7,601,166 B2 | 10/2009 | Biedermann et al. |
| 7,608,095 B2 | 10/2009 | Yuan et al. |
| 7,608,106 B2 | 10/2009 | Reiley |
| 7,611,526 B2 | 11/2009 | Carl et al. |
| 7,615,068 B2 | 11/2009 | Timm et al. |
| 7,625,394 B2 | 12/2009 | Molz, IV et al. |
| 7,625,396 B2 | 12/2009 | Jackson |
| 7,635,379 B2 | 12/2009 | Callahan et al. |
| 7,648,520 B2 | 1/2010 | Markworth |
| 7,648,522 B2 | 1/2010 | David |
| 7,662,172 B2 | 2/2010 | Warnick |
| 7,662,173 B2 | 2/2010 | Cragg et al. |
| 7,662,175 B2 | 2/2010 | Jackson |
| 7,674,293 B2 | 3/2010 | Kuiper et al. |
| 7,678,136 B2 | 3/2010 | Doubler et al. |
| 7,678,137 B2 | 3/2010 | Butler et al. |
| 7,682,377 B2 | 3/2010 | Konieczynski et al. |
| 7,691,129 B2 | 4/2010 | Felix |
| 7,691,132 B2 | 4/2010 | Landry et al. |
| 7,699,873 B2 | 4/2010 | Stevenson et al. |
| 7,699,875 B2 | 4/2010 | Timm |
| 7,704,270 B2 | 4/2010 | De Coninck |
| 7,708,762 B2 | 5/2010 | McCarthy et al. |
| 7,713,287 B2 | 5/2010 | Timm et al. |
| 7,713,288 B2 | 5/2010 | Timm et al. |
| 7,717,939 B2 | 5/2010 | Ludwig et al. |
| 7,722,646 B2 | 5/2010 | Ralph et al. |
| 7,722,649 B2 | 5/2010 | Biedermann et al. |
| 7,722,654 B2 | 5/2010 | Taylor et al. |
| 7,727,259 B2 | 6/2010 | Park |
| 7,727,261 B2 | 6/2010 | Barker et al. |
| 7,731,734 B2 | 6/2010 | Clement et al. |
| 7,731,736 B2 | 6/2010 | Guenther et al. |
| 7,763,051 B2 | 7/2010 | Labrom et al. |
| 7,763,052 B2 | 7/2010 | Jahng |
| 7,766,944 B2 | 8/2010 | Metz-Stavenhagen |
| 7,766,945 B2 | 8/2010 | Nilsson et al. |
| 7,776,071 B2 | 8/2010 | Fortin et al. |
| 7,785,350 B2 | 8/2010 | Eckhardt et al. |
| 7,785,354 B2 | 8/2010 | Biedermann et al. |
| 7,789,896 B2 | 9/2010 | Jackson |
| 7,794,477 B2 | 9/2010 | Melkent et al. |
| 7,794,481 B2 | 9/2010 | Molz, IV et al. |
| 7,799,060 B2 | 9/2010 | Lange et al. |
| 7,803,189 B2 | 9/2010 | Koske |
| 7,806,913 B2 | 10/2010 | Fanger et al. |
| 7,806,914 B2 | 10/2010 | Boyd et al. |
| 7,811,288 B2 | 10/2010 | Jones et al. |
| 7,811,309 B2 | 10/2010 | Timm et al. |
| 7,811,311 B2 | 10/2010 | Markworth et al. |
| 7,815,664 B2 | 10/2010 | Sherman et al. |
| 7,815,665 B2 | 10/2010 | Jahng et al. |
| 7,819,899 B2 | 10/2010 | Lancial |
| 7,819,901 B2 | 10/2010 | Yuan et al. |
| 7,819,902 B2 | 10/2010 | Abdelgany et al. |
| 7,824,431 B2 | 11/2010 | McCormack |
| 7,828,824 B2 | 11/2010 | Kwak et al. |
| 7,828,825 B2 | 11/2010 | Bruneau et al. |
| 7,828,826 B2 | 11/2010 | Drewry et al. |
| 7,828,830 B2 | 11/2010 | Thramann et al. |
| 7,833,250 B2 | 11/2010 | Jackson |
| 7,833,256 B2 | 11/2010 | Biedermann et al. |
| 7,842,072 B2 | 11/2010 | Dawson |
| 7,850,715 B2 | 12/2010 | Bonouskou et al. |
| 7,850,718 B2 | 12/2010 | Bette et al. |
| 7,854,752 B2 | 12/2010 | Colleran et al. |
| 7,857,833 B2 | 12/2010 | Abdou |
| 7,857,834 B2 | 12/2010 | Boschert |
| 7,862,586 B2 | 1/2011 | Malek |
| 7,862,587 B2 | 1/2011 | Jackson |
| 7,862,588 B2 | 1/2011 | Abdou |
| 7,862,591 B2 | 1/2011 | Dewey et al. |
| 7,862,594 B2 | 1/2011 | Abdelgany |
| 7,871,413 B2 | 1/2011 | Park et al. |
| 7,875,059 B2 | 1/2011 | Patterson et al. |
| 7,875,060 B2 | 1/2011 | Chin |
| 7,879,074 B2 | 2/2011 | Kwak et al. |
| 7,892,266 B2 | 2/2011 | Carli |
| 7,909,856 B2 | 3/2011 | Yuan et al. |
| 7,914,558 B2 | 3/2011 | Landry et al. |
| 7,918,792 B2 | 4/2011 | Drzyzga et al. |
| 7,927,359 B2 | 4/2011 | Trautwein |
| 7,931,675 B2 | 4/2011 | Panjabi et al. |
| 7,942,900 B2 | 5/2011 | Winslow et al. |
| 7,942,910 B2 | 5/2011 | Doubler et al. |
| 7,963,978 B2 | 6/2011 | Winslow et al. |
| 7,985,243 B2 | 7/2011 | Winslow et al. |
| 7,993,372 B2 | 8/2011 | Winslow et al. |
| 8,002,800 B2 | 8/2011 | Winslow et al. |
| 8,002,803 B2 | 8/2011 | Winslow et al. |
| 8,007,518 B2 | 8/2011 | Winslow et al. |
| 8,012,175 B2 | 9/2011 | Winslow et al. |
| 8,012,181 B2 | 9/2011 | Winslow et al. |
| 8,016,861 B2 | 9/2011 | Mitchell et al. |
| 8,021,396 B2 | 9/2011 | Winslow et al. |
| 8,043,337 B2 | 10/2011 | Klyce et al. |
| 8,048,113 B2 | 11/2011 | Winslow et al. |
| 8,048,115 B2 | 11/2011 | Winslow et al. |
| 8,048,121 B2 | 11/2011 | Mitchell et al. |
| 8,048,122 B2 | 11/2011 | Mitchell et al. |
| 8,048,123 B2 | 11/2011 | Mitchell et al. |
| 8,048,125 B2 | 11/2011 | Mitchell et al. |
| 8,048,128 B2 | 11/2011 | Klyce et al. |
| 8,052,721 B2 | 11/2011 | Winslow et al. |
| 8,052,722 B2 | 11/2011 | Winslow et al. |
| 8,057,514 B2 | 11/2011 | Winslow et al. |
| 8,057,515 B2 | 11/2011 | Flynn et al. |
| 8,057,517 B2 | 11/2011 | Flynn et al. |
| 8,070,774 B2 | 12/2011 | Winslow et al. |
| 8,070,775 B2 | 12/2011 | Winslow et al. |
| 8,070,776 B2 | 12/2011 | Winslow et al. |
| 8,070,780 B2 | 12/2011 | Winslow et al. |
| 8,080,039 B2 | 12/2011 | Zucherman et al. |
| 2002/0143327 A1 | 10/2002 | Shluzas |

| | | | | | | |
|---|---|---|---|---|---|---|
| 2002/0151895 A1 | 10/2002 | Soboleski et al. | | 2006/0149380 A1 | 7/2006 | Lotz et al. |
| 2003/0004511 A1 | 1/2003 | Ferree | | 2006/0161153 A1 | 7/2006 | Hawkes et al. |
| 2003/0171749 A1 | 9/2003 | Le Couedic et al. | | 2006/0195093 A1 | 8/2006 | Jahng |
| 2004/0015166 A1 | 1/2004 | Gorek | | 2006/0200128 A1 | 9/2006 | Mueller |
| 2004/0034374 A1 | 2/2004 | Zatzsch et al. | | 2006/0200131 A1 | 9/2006 | Chao et al. |
| 2004/0049285 A1 | 3/2004 | Haas | | 2006/0229607 A1 | 10/2006 | Brumfield |
| 2004/0097925 A1 | 5/2004 | Boehm, Jr. et al. | | 2006/0229613 A1 | 10/2006 | Timm et al. |
| 2004/0111088 A1 | 6/2004 | Picetti et al. | | 2006/0235385 A1 | 10/2006 | Whipple |
| 2004/0122425 A1 | 6/2004 | Suzuki et al. | | 2006/0235389 A1 | 10/2006 | Albert et al. |
| 2004/0147928 A1 | 7/2004 | Landry et al. | | 2006/0235392 A1 | 10/2006 | Hammer et al. |
| 2004/0153077 A1 | 8/2004 | Biedermann et al. | | 2006/0235393 A1 | 10/2006 | Bono et al. |
| 2004/0158247 A1 | 8/2004 | Sitiso et al. | | 2006/0241600 A1 | 10/2006 | Ensign et al. |
| 2004/0162560 A1 | 8/2004 | Raynor et al. | | 2006/0241601 A1 | 10/2006 | Trautwein et al. |
| 2004/0172022 A1 | 9/2004 | Landry et al. | | 2006/0241603 A1 | 10/2006 | Jackson |
| 2004/0172024 A1 | 9/2004 | Gorek | | 2006/0241757 A1 | 10/2006 | Anderson |
| 2004/0215192 A1 | 10/2004 | Justis et al. | | 2006/0247623 A1 | 11/2006 | Anderson et al. |
| 2004/0225289 A1 | 11/2004 | Biedermann et al. | | 2006/0247631 A1 | 11/2006 | Ahn et al. |
| 2004/0230192 A1 | 11/2004 | Graf | | 2006/0247637 A1 | 11/2006 | Colleran et al. |
| 2004/0230304 A1 | 11/2004 | Yuan et al. | | 2006/0253118 A1 | 11/2006 | Bailey |
| 2005/0049589 A1 | 3/2005 | Jackson | | 2006/0264935 A1 | 11/2006 | White |
| 2005/0080415 A1 | 4/2005 | Keyer et al. | | 2006/0264937 A1 | 11/2006 | White |
| 2005/0080486 A1 | 4/2005 | Fallin et al. | | 2006/0276897 A1 | 12/2006 | Winslow et al. |
| 2005/0090822 A1 | 4/2005 | DiPoto | | 2006/0282073 A1 | 12/2006 | Simanovsky |
| 2005/0096652 A1 | 5/2005 | Burton | | 2006/0282078 A1 | 12/2006 | Labrom et al. |
| 2005/0107788 A1 | 5/2005 | Beaurain et al. | | 2007/0016190 A1 | 1/2007 | Martinez et al. |
| 2005/0113923 A1 | 5/2005 | Acker et al. | | 2007/0016194 A1 | 1/2007 | Shaolian et al. |
| 2005/0131404 A1 | 6/2005 | Mazda et al. | | 2007/0016201 A1 | 1/2007 | Freudiger |
| 2005/0131406 A1 | 6/2005 | Reiley et al. | | 2007/0049936 A1 | 3/2007 | Colleran et al. |
| 2005/0143737 A1 | 6/2005 | Pafford et al. | | 2007/0083200 A1 | 4/2007 | Gittings et al. |
| 2005/0171537 A1 | 8/2005 | Mazel et al. | | 2007/0088359 A1 | 4/2007 | Woods et al. |
| 2005/0171543 A1 | 8/2005 | Timm et al. | | 2007/0093814 A1 | 4/2007 | Callahan, II et al. |
| 2005/0177156 A1 | 8/2005 | Timm et al. | | 2007/0093820 A1 | 4/2007 | Freudiger |
| 2005/0177157 A1 | 8/2005 | Jahng | | 2007/0093821 A1 | 4/2007 | Freudiger |
| 2005/0177164 A1 | 8/2005 | Walters et al. | | 2007/0118122 A1 | 5/2007 | Butler et al. |
| 2005/0182400 A1 | 8/2005 | White | | 2007/0123860 A1* | 5/2007 | Francis et al. ................ 606/61 |
| 2005/0182401 A1 | 8/2005 | Timm et al. | | 2007/0123871 A1 | 5/2007 | Jahng |
| 2005/0192569 A1 | 9/2005 | Nichols et al. | | 2007/0161994 A1 | 7/2007 | Lowery et al. |
| 2005/0228378 A1 | 10/2005 | Kalfas et al. | | 2007/0162007 A1 | 7/2007 | Shoham |
| 2005/0228382 A1 | 10/2005 | Richelsoph et al. | | 2007/0167946 A1 | 7/2007 | Triplett et al. |
| 2005/0228385 A1 | 10/2005 | Iott et al. | | 2007/0167947 A1 | 7/2007 | Gittings |
| 2005/0240180 A1 | 10/2005 | Vienney et al. | | 2007/0198014 A1 | 8/2007 | Graf et al. |
| 2005/0240265 A1 | 10/2005 | Kuiper et al. | | 2007/0213719 A1 | 9/2007 | Hudgins et al. |
| 2005/0261770 A1 | 11/2005 | Kuiper et al. | | 2007/0233068 A1 | 10/2007 | Bruneau et al. |
| 2005/0267470 A1 | 12/2005 | McBride | | 2007/0233072 A1 | 10/2007 | Dickinson et al. |
| 2005/0267579 A1 | 12/2005 | Reiley et al. | | 2007/0233090 A1 | 10/2007 | Naifeh et al. |
| 2005/0277922 A1 | 12/2005 | Trieu et al. | | 2007/0233091 A1 | 10/2007 | Naifeh et al. |
| 2005/0288670 A1 | 12/2005 | Panjabi et al. | | 2007/0233092 A1 | 10/2007 | Falahee |
| 2006/0025771 A1 | 2/2006 | Jackson | | 2007/0233093 A1 | 10/2007 | Falahee |
| 2006/0036324 A1 | 2/2006 | Sachs et al. | | 2007/0233094 A1 | 10/2007 | Colleran et al. |
| 2006/0052783 A1 | 3/2006 | Dant et al. | | 2007/0250061 A1 | 10/2007 | Chin et al. |
| 2006/0052784 A1 | 3/2006 | Dant et al. | | 2007/0270836 A1 | 11/2007 | Bruneau et al. |
| 2006/0052786 A1 | 3/2006 | Dant et al. | | 2007/0270838 A1 | 11/2007 | Bruneau et al. |
| 2006/0058787 A1 | 3/2006 | David | | 2007/0276380 A1 | 11/2007 | Jahng et al. |
| 2006/0058788 A1 | 3/2006 | Hammer et al. | | 2007/0288009 A1 | 12/2007 | Brown et al. |
| 2006/0079894 A1 | 4/2006 | Colleran et al. | | 2007/0288012 A1 | 12/2007 | Colleran et al. |
| 2006/0079896 A1 | 4/2006 | Kwak et al. | | 2008/0009864 A1 | 1/2008 | Forton et al. |
| 2006/0084978 A1 | 4/2006 | Mokhtar | | 2008/0021459 A1 | 1/2008 | Lim |
| 2006/0084982 A1 | 4/2006 | Kim | | 2008/0021461 A1 | 1/2008 | Barker et al. |
| 2006/0084983 A1 | 4/2006 | Kim | | 2008/0033433 A1 | 2/2008 | Implicito |
| 2006/0084984 A1 | 4/2006 | Kim | | 2008/0039838 A1 | 2/2008 | Landry et al. |
| 2006/0084985 A1 | 4/2006 | Kim | | 2008/0051787 A1 | 2/2008 | Remington et al. |
| 2006/0084987 A1 | 4/2006 | Kim | | 2008/0065073 A1 | 3/2008 | Perriello et al. |
| 2006/0084988 A1 | 4/2006 | Kim | | 2008/0065075 A1 | 3/2008 | Dant et al. |
| 2006/0084989 A1 | 4/2006 | Dickinson et al. | | 2008/0065079 A1 | 3/2008 | Bruneau et al. |
| 2006/0084990 A1 | 4/2006 | Gournay et al. | | 2008/0071273 A1 | 3/2008 | Hawkes et al. |
| 2006/0085069 A1 | 4/2006 | Kim | | 2008/0077139 A1 | 3/2008 | Landry et al. |
| 2006/0085070 A1 | 4/2006 | Kim | | 2008/0183215 A1 | 7/2008 | Altarac et al. |
| 2006/0089643 A1 | 4/2006 | Mujwid | | 2008/0195208 A1 | 8/2008 | Castellvi et al. |
| 2006/0095035 A1 | 5/2006 | Jones et al. | | 2008/0262554 A1 | 10/2008 | Hayes et al. |
| 2006/0106383 A1 | 5/2006 | Biedermann et al. | | 2008/0312693 A1 | 12/2008 | Trautwein et al. |
| 2006/0111712 A1 | 5/2006 | Jackson | | 2009/0062868 A1 | 3/2009 | Casutt |
| 2006/0122620 A1 | 6/2006 | Kim | | 2010/0174317 A1 | 7/2010 | Timm et al. |
| 2006/0129148 A1 | 6/2006 | Simmons et al. | | 2010/0198270 A1 | 8/2010 | Barker et al. |
| 2006/0129149 A1 | 6/2006 | Iott et al. | | 2010/0222819 A1 | 9/2010 | Timm et al. |
| 2006/0142761 A1 | 6/2006 | Landry et al. | | | | |
| 2006/0149242 A1 | 7/2006 | Kraus et al. | | | FOREIGN PATENT DOCUMENTS | |
| 2006/0149244 A1 | 7/2006 | Amrein et al. | | EP | 0128058 B1 | 4/1988 |
| | | | | EP | 0669109 B1 | 8/1995 |

| | | |
|---|---|---|
| EP | 0982007 | 3/2000 |
| EP | 1281362 A2 | 2/2003 |
| EP | 1330987 A1 | 7/2003 |
| EP | 1737368 B1 | 12/2009 |
| EP | 2277465 | 1/2011 |
| FR | 2612070 A1 | 9/1988 |
| FR | 2615095 A1 | 11/1988 |
| FR | 2844180 A1 | 3/2004 |
| FR | 2880256 B1 | 7/2006 |
| GB | 780652 | 8/1957 |
| GB | 2173104 | 10/1986 |
| GB | 2382304 | 5/2003 |
| KR | 20080072848 | 8/2008 |
| KR | 20080084997 | 9/2008 |
| WO | WO 87/07134 | 12/1987 |
| WO | WO 94/21185 | 9/1994 |
| WO | WO 98/27884 | 7/1998 |
| WO | WO 01/45576 | 6/2001 |
| WO | WO 01/91656 | 12/2001 |
| WO | WO 02/07621 | 1/2002 |
| WO | WO 02/07622 | 1/2002 |
| WO | WO 02/17803 | 3/2002 |
| WO | WO 02/39921 | 5/2002 |
| WO | WO 02/43603 | 6/2002 |
| WO | WO 02/102259 | 12/2002 |
| WO | WO 03/007828 | 1/2003 |
| WO | WO 03/009737 | 2/2003 |
| WO | WO 03/015647 | 2/2003 |
| WO | WO 03/037216 | 5/2003 |
| WO | WO 03/077806 | 9/2003 |
| WO | WO2004/024011 | 3/2004 |
| WO | WO2004/034916 | 4/2004 |
| WO | WO2006/033503 | 3/2006 |
| WO | WO2006/066685 | 6/2006 |
| WO | WO2006/105935 | 10/2006 |
| WO | WO2007064324 | 6/2007 |
| WO | WO2007/080317 | 7/2007 |
| WO | WO2008/034130 | 3/2008 |
| WO | WO2008/073544 | 6/2008 |

OTHER PUBLICATIONS

Mekanika, Inc. Website, 2003; Mekanika—The Spinal Stabilization Company, product description for Modulus System, 2 pages, <http://mekanika.com/htm/modsystem.htm>.

Zimmer, Inc. Website, 2007; Zimmer Spine, product description for Dynesis—The Dynamic Stabilization System, 5 pages, <http://www.zimmer.com/ctl?template=IN&action=1&op=global&id=9165&pr=Y>.

Ito Medical Instrument website, 2006; ITOIKA Medical Instruments, product description for S-Plate, 15 pages, <http://ito-ika.co.jp/s-plate/splate1.pdf and http://ito-ika.co.jp/s-plate/splate1.pdf>.

"Flexible rods and the case for dynamic stabilization," Jason M. Highsmith, M.D., et al., Neurosurg. Focus, vol. 22, Jan. 2007, pp. 1-5.

"The Spinous Process: The Forgotten Appendage," Kenneth R. Kattan, M. D. eta l., Skeletal Radiology, vol. 6, 1981, pp. 199-204.

"Morphological and functional changes of the lumbar spinous processes in the elderly," R. Scapinelli, Surgical Radiologic Anatomy, vol. 11, 1989, pp. 129-133.

"The Paraspinal Sacrospinalis-Splitting Approach to the Lumbar Spine," Leon L. Wiltse et al., The Journal of Bone & Joint Surgery, vol. 50-A, No. 5, Jul. 1968 pp. 919-926.

Dynamic Reconstruction of the Spine, D.H. Kim et al., Thieme, New York 2006, Chapters 1, 2, 30, 31, 37-43.

International Search Report for PCT/US07/70981 dated Apr. 23, 2008, 7 pages.

International Search Report for PCT/US/2009/058466 dated Apr. 29, 2010, 13 pages.

International Search Report for PCT/US/2009/058460 dated Apr. 29, 2010, 11 pages.

International Search Report for PCT/US/2009/058470 dated Apr. 29, 2010, 12 pages.

International Search Report for PCT/US/2009/066567 dated Jul. 20, 2010, 9 pages.

International Search Report for PCT/US2010/058776 dated Aug. 23, 2011, 4 pages.

* cited by examiner

FIG. 3A
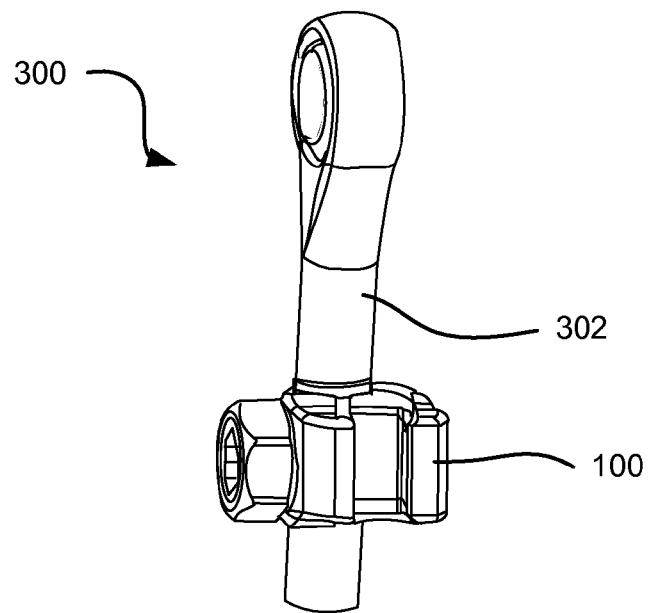
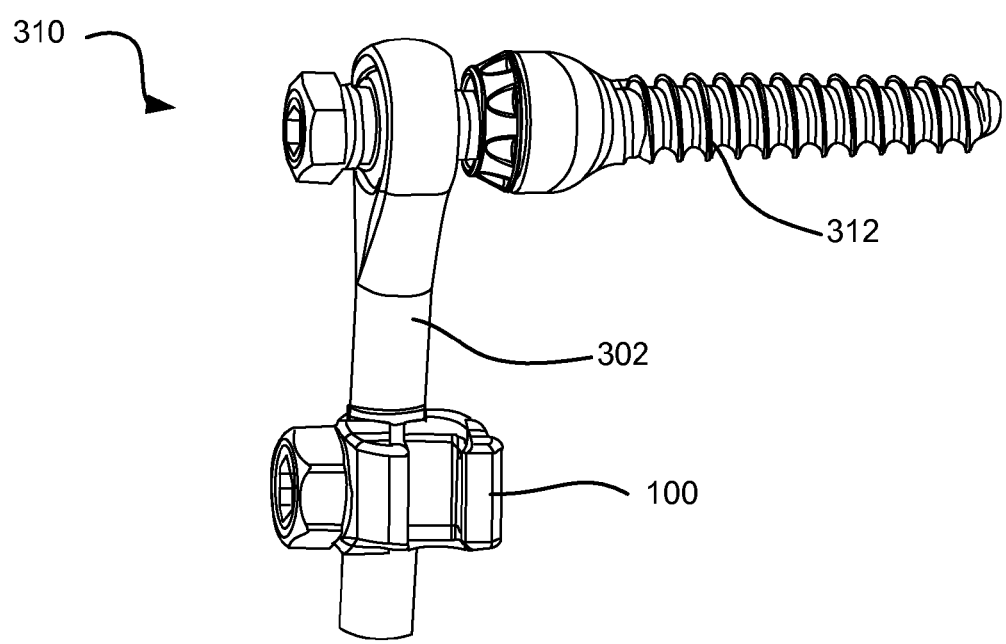
FIG. 3B

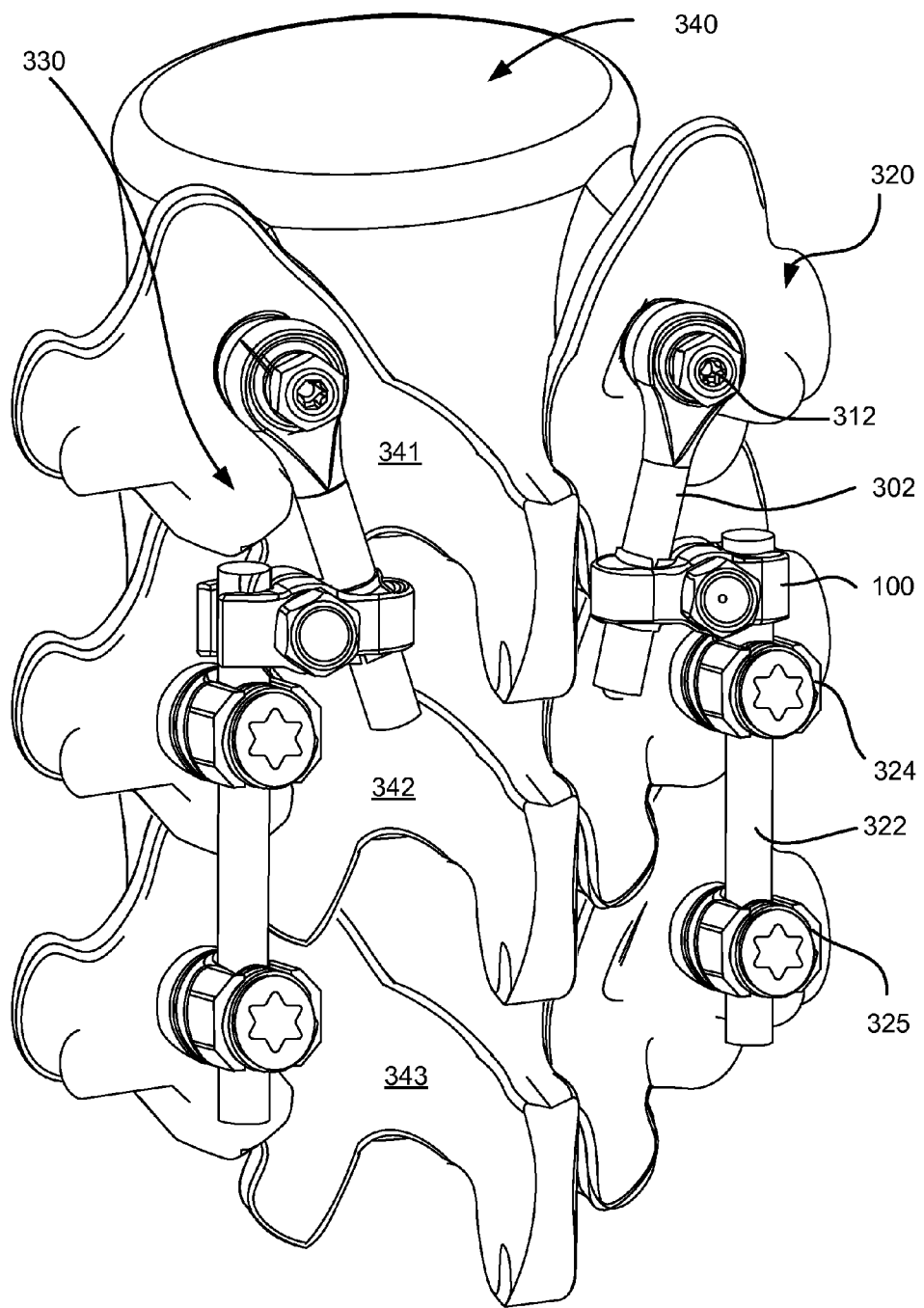

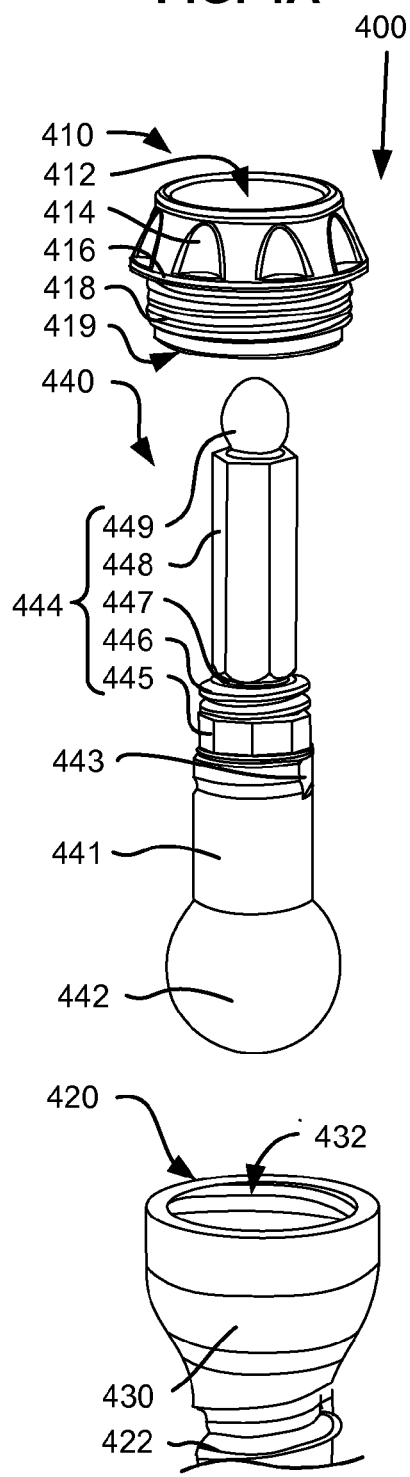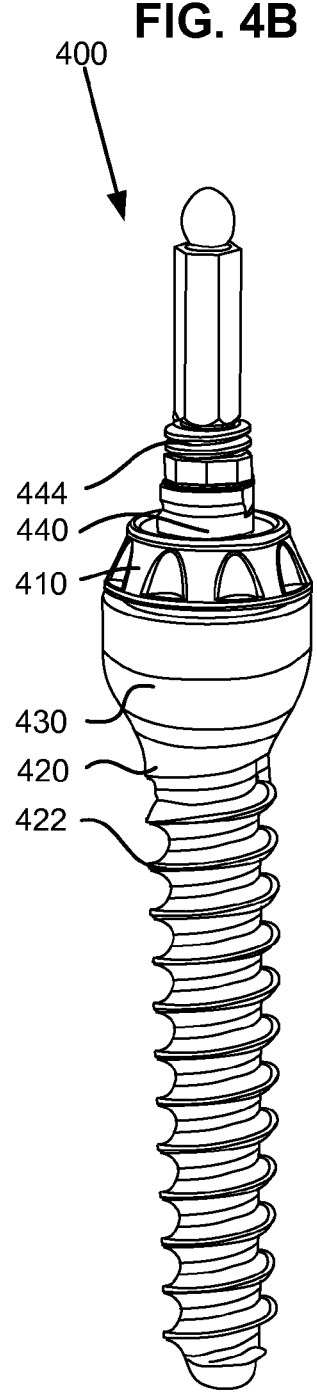
FIG. 4A
FIG. 4B

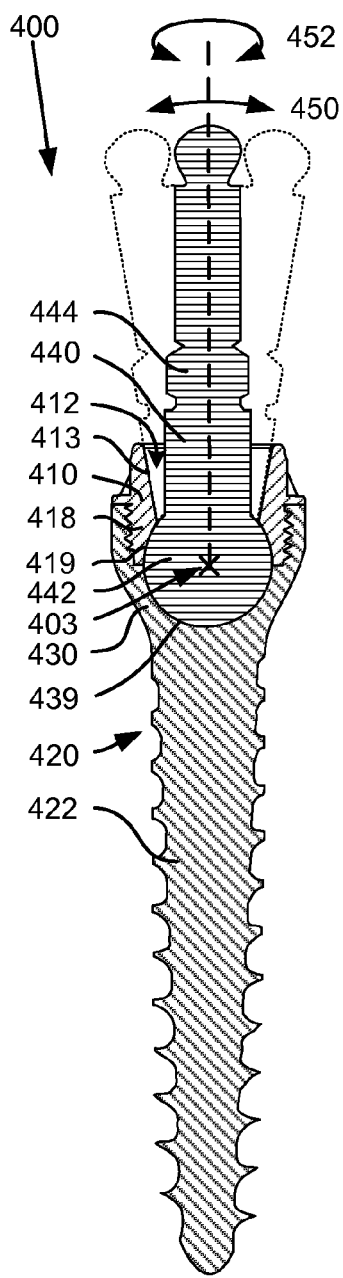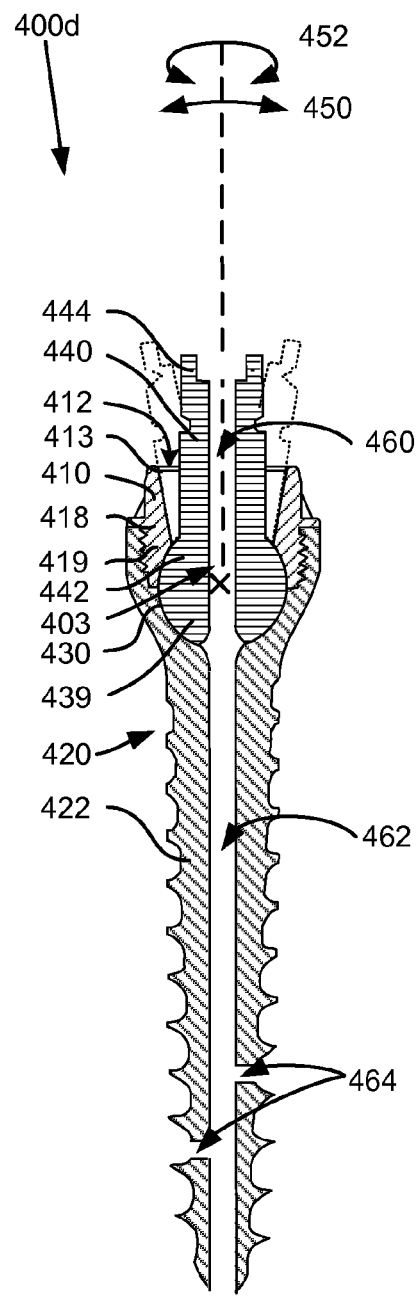

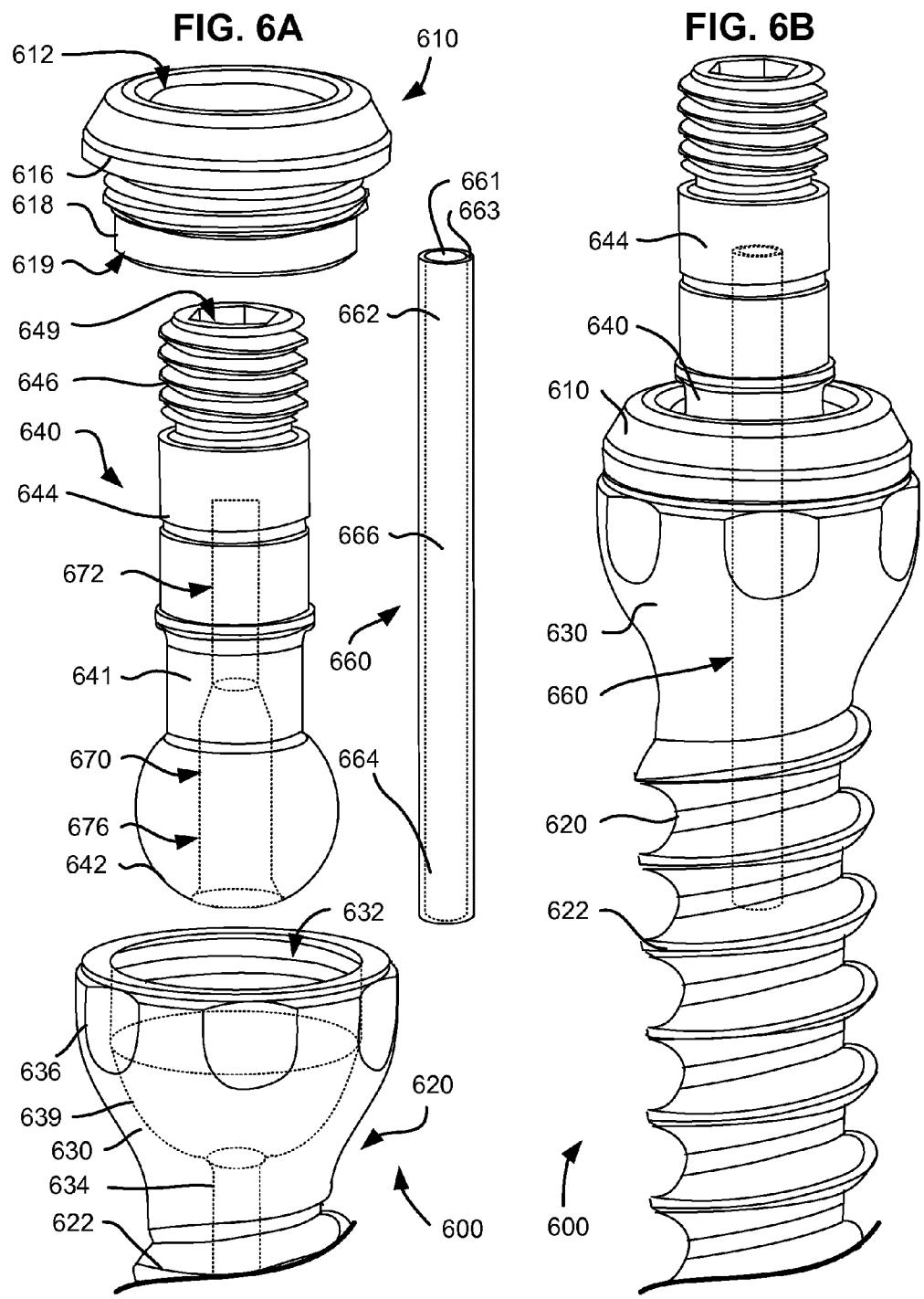

FIG. 6C
FIG. 6D
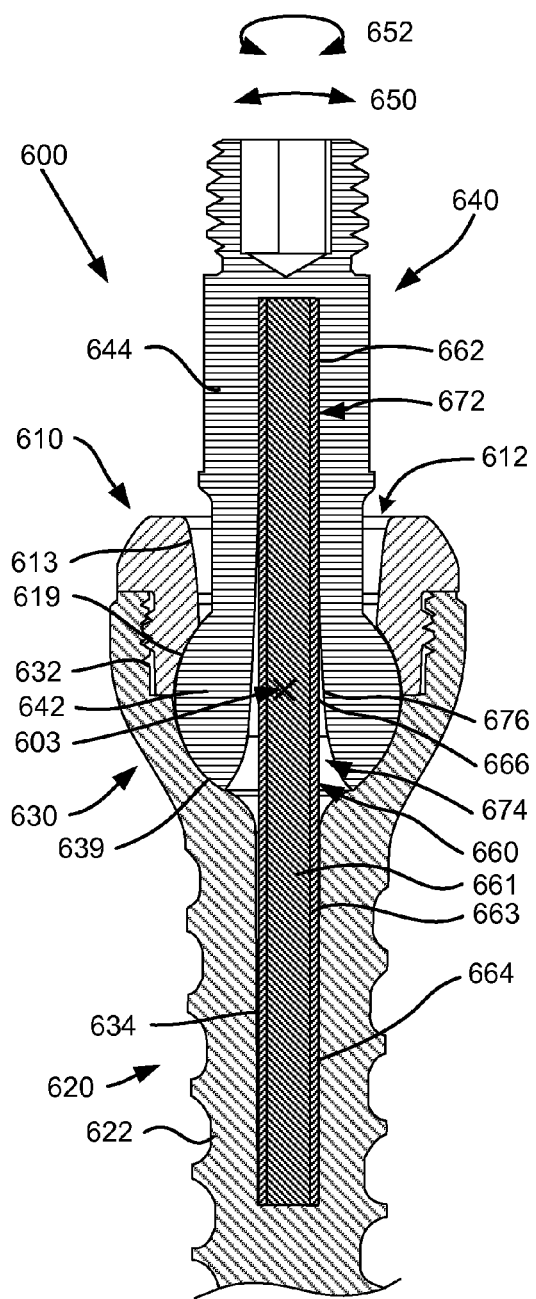
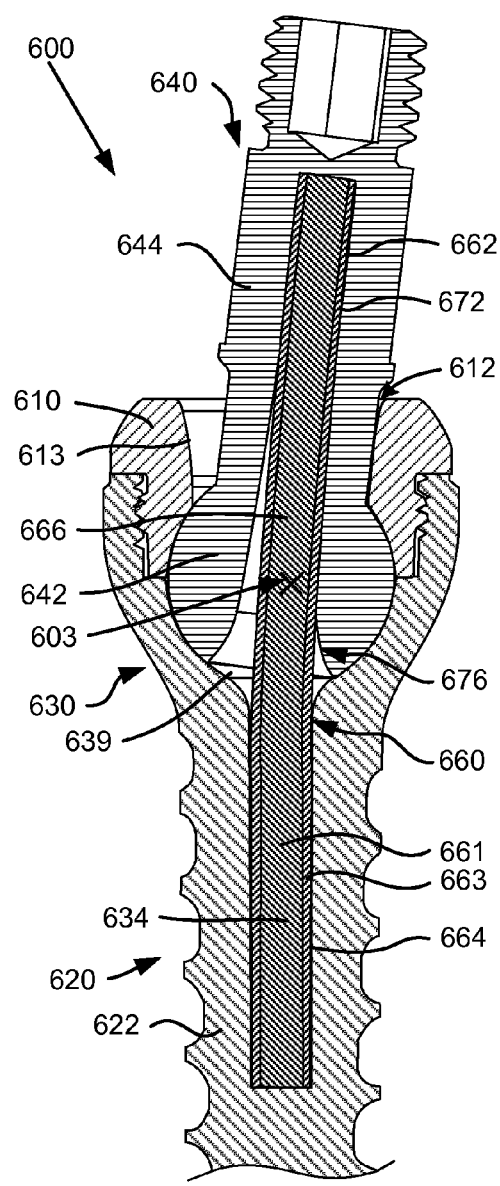

SPINAL ROD CONNECTORS, METHODS OF USE, AND SPINAL PROSTHESIS INCORPORATING SPINAL ROD CONNECTORS

CROSS-REFERENCES TO RELATED APPLICATIONS

This application is related to all of the following applications including:

U.S. patent application Ser. No. 12/566,478, filed Sep. 24, 2009, entitled "Modular In-Line Deflection Rod And Bone Anchor System And Method For Dynamic Stabilization Of The Spine";

U.S. patent application Ser. No. 12/566,485, filed Sep. 24, 2009, entitled "Versatile Polyaxial Connector Assembly And Method For Dynamic Stabilization Of The Spine";

U.S. patent application Ser. No. 12/566,487, filed Sep. 24, 2009, entitled "Versatile Offset Polyaxial Connector And Method For Dynamic Stabilization Of The Spine";

U.S. patent application Ser. No. 12/566,494, filed Sep. 24, 2009, entitled "Load-Sharing Component Having A Deflectable Post And Method For Dynamic Stabilization Of The Spine";

U.S. patent application Ser. No. 12/566,498, filed Sep. 24, 2009, entitled "Load-Sharing Bone Anchor Having A Durable Compliant Member And Method For Dynamic Stabilization Of The Spine";

U.S. patent application Ser. No. 12/566,504, filed Sep. 24, 2009, entitled "Load-Sharing Bone Anchor Having A Deflectable Post With A Compliant Ring And Method For Stabilization Of The Spine";

U.S. patent application Ser. No. 12/566,507, filed Sep. 24, 2009, entitled "Load-Sharing Bone Anchor Having A Deflectable Post With A Compliant Ring And Method For Stabilization Of The Spine";

U.S. patent application Ser. No. 12/566,511, filed Sep. 24, 2009, entitled "Load-Sharing Bone Anchor Having A Deflectable Post And Method For Stabilization Of The Spine";

U.S. patent application Ser. No. 12/566,516, filed Sep. 24, 2009, entitled "Load-Sharing Bone Anchor Having A Natural Center Of Rotation And Method For Dynamic Stabilization Of The Spine";

U.S. patent application Ser. No. 12/566,519, filed Sep. 24, 2009, entitled "Dynamic Spinal Rod And Method For Dynamic Stabilization Of The Spine";

U.S. patent application Ser. No. 12/566,522, filed Sep. 24, 2009, entitled "Dynamic Spinal Rod Assembly And Method For Dynamic Stabilization Of The Spine";

U.S. patent application Ser. No. 12/566,529, filed Sep. 24, 2009, entitled "Configurable Dynamic Spinal Rod And Method For Dynamic Stabilization Of The Spine";

U.S. patent application Ser. No. 12/566,531, filed Sep. 24, 2009, entitled "A Spinal Prosthesis Having A Three Bar Linkage For Motion Preservation And Dynamic Stabilization Of The Spine";

U.S. patent application Ser. No. 12/566,534, filed Sep. 24, 2009, entitled "Surgical Tool And Method For Implantation of A Dynamic Bone Anchor";

U.S. patent application Ser. No. 12/566,547, filed Sep. 24, 2009, entitled "Surgical Tool And Method For Connecting A Dynamic Bone Anchor and Dynamic Vertical Rod";

U.S. patent application Ser. No. 12/566,551, filed Sep. 24, 2009, entitled "Load-Sharing Bone Anchor Having A Deflectable Post And Centering Spring And Method For Dynamic Stabilization Of The Spine";

U.S. patent application Ser. No. 12/566,553, filed Sep. 24, 2009, entitled "Load-Sharing Component Having A Deflectable Post And Centering Spring And Method For Dynamic Stabilization Of The Spine";

U.S. patent application Ser. No. 12/566,559, filed Sep. 24, 2009, entitled "Load-Sharing Bone Anchor Having A Deflectable Post And Axial Spring And Method For Dynamic Stabilization Of The Spine";

U.S. patent application Ser. No. 12/629,811, filed Dec. 2, 2009, entitled "Low Profile Spinal Prosthesis Incorporating A Bone Anchor Having A Deflectable Post And A Compound Spinal Rod";

International Patent Application No. PCT/US2009/066567, filed Dec. 3, 3009, entitled "Low Profile Spinal Prosthesis Incorporating A Bone Anchor Having A Deflectable Post And A Compound Spinal Rod"; and U.S. patent application Ser. No. 13/206,286, filed Aug. 9, 2011, entitled "Low Profile Spinal Prosthesis Incorporating a Cannulated Bone Anchor Having a Deflectable Post and a Compound Spinal Rod" and which is a continuation-in-part of U.S. patent application Ser. No. 13/098,280, filed Apr. 29, 2011, entitled "Low Profile Spinal Prosthesis Incorporating A Bone Anchor Having A Deflectable Post And A Compound Spinal Rod" and which is a continuation-in-part of U.S. patent application Ser. No. 12/959,200, filed Dec. 2, 2010, entitled "Low Profile Spinal Prosthesis Incorporating A Bone Anchor Having A Deflectable Post And A Compound Spinal Rod".

All of the afore-mentioned patent applications are incorporated herein by reference in their entireties.

BACKGROUND OF INVENTION

Back pain is a significant clinical problem and the costs to treat it, both surgical and medical, are estimated to be over $2 billion per year. One method for treating a broad range of degenerative spinal disorders is spinal fusion. Implantable medical devices designed to fuse vertebrae of the spine to treat have developed rapidly over the last decade. However, spinal fusion has several disadvantages including reduced range of motion and accelerated degenerative changes adjacent the fused vertebrae.

Alternative devices and treatments have been developed for treating degenerative spinal disorders while preserving motion. These devices and treatments offer the possibility of treating degenerative spinal disorders without the disadvantages of spinal fusion. However, current devices and treatments suffer from disadvantages e.g., complicated implantation procedures; lack of flexibility to conform to diverse patient anatomy; the need to remove tissue and bone for implantation; increased stress on spinal anatomy; insecure anchor systems; poor durability, and poor revision options. Consequently, there is a need for new and improved devices and methods for treating degenerative spinal disorders while preserving motion.

SUMMARY OF INVENTION

The present invention includes a spinal implant system and methods that can dynamically stabilize the spine while providing for the preservation of spinal motion. Embodiments of the invention provide a dynamic stabilization system which includes: versatile components, adaptable stabilization assemblies, and methods of implantation. An aspect of embodiments of the invention is the ability to dynamically stabilize a level of the spine adjacent to one or more immobilized/fused levels of the spine and thereby prevent or reduce accelerated degenerative changes adjacent the fused vertebrae. Another aspect of the invention is to facilitate the process of implantation and minimize disruption of tissues during implantation.

Embodiments of the present invention include a spinal rod connector that is adapted to connect two spinal rods. Embodiments of the spinal rod connector include first and second channels which are defined in a housing. The first and second channels can be urged together in order to capture first and second spinal rods when a fastener is actuated. Embodiments of the present invention allow the first and second rods to be positioned relative to each other in one of a parallel and a non-parallel manner prior to the fastener locking the first and second spinal rods in position.

Thus, the present invention provides new and improved systems, devices and methods for treating degenerative spinal disorders by connecting a dynamic spinal stabilization assembly to a spinal fusion assembly. The dynamic stabilization assembly supports the spine while preserving motion thereby preventing or reducing accelerated degenerative changes adjacent the fused vertebrae. These and other objects, features and advantages of the invention will be apparent from the drawings and detailed description which follow.

BRIEF DESCRIPTION OF THE DRAWINGS

FIG. 3A illustrates a spinal subassembly utilizing the spinal rod connector of FIG. 1A according to an embodiment of the invention.

FIG. 3B illustrates another spinal subassembly utilizing the spinal rod connector of FIG. 1A according to an embodiment of the invention.

FIG. 3D illustrates a pair of spinal prostheses utilizing the spinal rod connector of FIG. 1A implanted in the spine according to an embodiment of the invention.

FIG. 4A shows an exploded view of a dynamic bone anchor suitable for use with the rod connectors of FIGS. 1A and 2A according to embodiments of the invention.

FIG. 4B shows a perspective view of the dynamic bone anchor of FIG. 4A as assembled.

FIG. 4C shows a sectional view of the dynamic bone anchor of FIG. 4A as assembled.

FIG. 4D shows a sectional view of a cannulated variant of the dynamic bone anchor of FIG. 4A as assembled.

FIG. 6A shows an exploded view of an alternative dynamic bone anchor suitable for use with the rod connectors of FIGS. 1A and 2A according to embodiments of the invention.

FIG. 6B shows a perspective view of the alternative dynamic bone anchor of FIG. 8A as assembled.

FIG. 6C shows a sectional view of the alternative dynamic bone anchor of FIG. 8A.

FIG. 6D shows a sectional view of the alternative dynamic bone anchor of FIG. 10A as assembled and illustrating deflection of the deflectable post.

DETAILED DESCRIPTION OF THE PREFERRED EMBODIMENTS

Figure 1A:
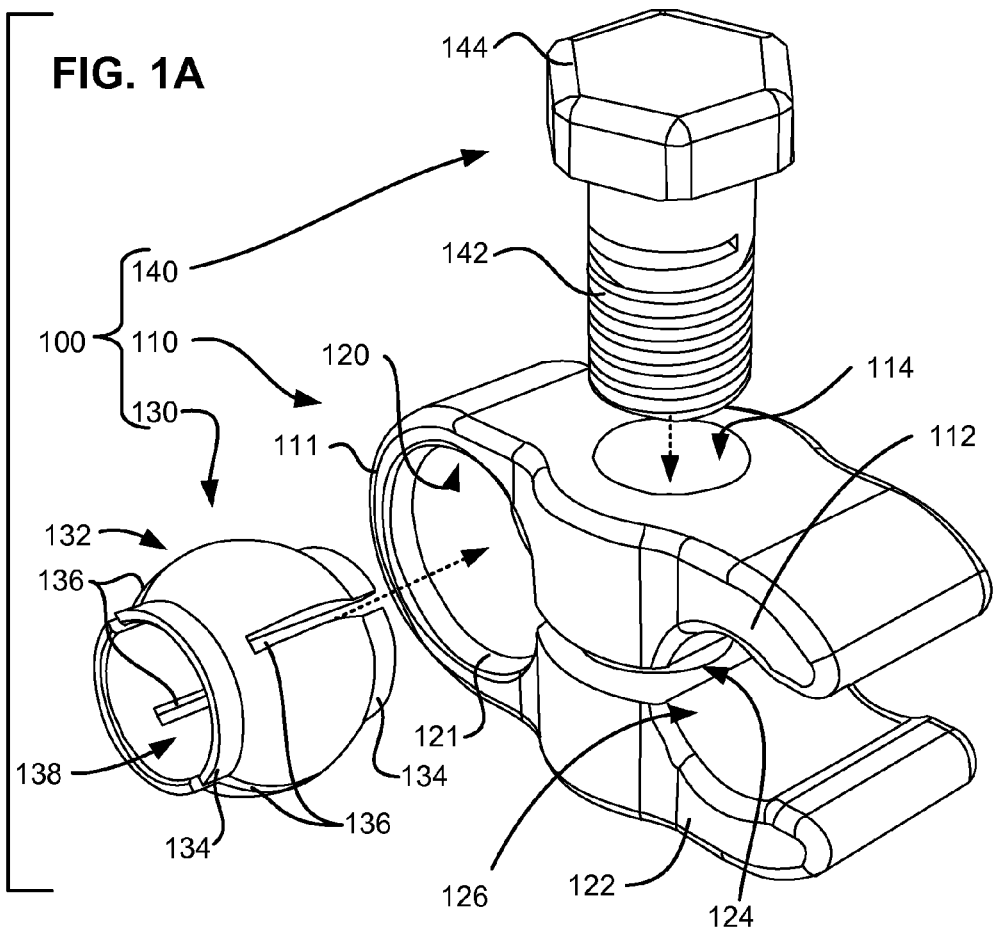
FIG. 1A shows an exploded view of a rod connector according to an embodiment of the invention.

The present invention includes a rod connector system and methods which can dynamically stabilize the spine while providing for the preservation of spinal motion. Alternative embodiments can be used for spinal fusion. An aspect of the invention is restoring and/or preserving the natural motion of the spine including the quality of motion as well as the range of motion. Still, another aspect of the invention is providing for load sharing and stabilization of the spine while preserving motion. Still another aspect is providing for the connection of load sharing and stabilization components to a spinal rod spanning fused levels of the spine. Still another aspect is providing for the connection of load sharing and stabilization components to a spinal rod spanning fused levels of the spine in order to prevent/reduce accelerated degeneration of the adjacent non-fused level or levels of the spine.

Another aspect of the invention is to provide a modular system which can be customized to the needs of the patient. Embodiments of the invention allow for fused levels to be placed next to dynamically stabilized levels. Such embodiments of the invention enable vertebral levels adjacent to fusion levels to be shielded by providing a transition from a rigid fusion level to a dynamically stable, motion preserved, and more mobile level.

Embodiments of the present invention provide for assembly of a dynamic stabilization system which supports the spine while providing for the preservation of spinal motion. The dynamic stabilization system has an anchor system, a deflection system, a vertical rod system and a connection system. The anchor system anchors the construct to the spinal anatomy. The deflection system provides dynamic stabilization while reducing the stress exerted upon the bone anchors and spinal anatomy. The vertical rod system connects different levels of the construct in a multilevel assembly and may in some embodiments include compound deflection rods. The connection system includes rod connectors which adjustably connect components of the vertical rod system allowing for appropriate, efficient and convenient placement of the anchor system and deflection system relative to the spine. Embodiments can enable vertebral levels adjacent to fusion levels to be shielded by providing a transition from a rigid fusion level to a dynamically stable, motion preserved, and more mobile level at the time the fusion is performed or as part of a revision procedure to prevent/reduce accelerated degeneration of the adjacent non-fused level or levels of the spine.

Embodiments of the invention include a construct with an anchor system, a deflection system, a vertical rod system and a connection system. The deflection system provides dynamic stabilization while reducing the stress exerted upon the bone anchors and spinal anatomy. The anchor system anchors the deflection system to the spine. The connection system connects components of the vertical rod system. The vertical rod system connects the dynamic stabilization system and anchor system components on different vertebra to provide load sharing and dynamic stabilization.

Embodiments of the present invention include a rod connector which allows for the adjustable connection of two substantially parallel vertical spinal rods. The rod connector includes a housing and includes two channels to receive vertical spinal rods. A first channel passes through a compression ball and is generally cylindrical and adapted to receive a vertical rod inserted axially. A second channel is cylindrical but has a gap through which a vertical rod can be received laterally into the second channel. The rod connector housing includes a bolt which passes through the housing between the two channels. Tightening of the bolt causes compression of the housing causing the compression ball to reduce the diameter of the first channel thereby securing the compression ball to a vertical rod received therein. Tightening of the bolt also causes compression of the gap in the second channel thereby reducing the diameter of the second channel and thereby securing the housing to a vertical rod received in the second channel.

Embodiments of the present invention include a rod connector and a compound spinal rod which preserves range of motion and reduces stress exerted upon the bone anchors and spinal anatomy. The rod of the compound spinal rod is inserted in the first channel of the rod connector. The second channel of the rod connector is adapted to receive a vertical rod such that the rod connector can be adjustable to secure the compound spinal rod to the vertical rod. The compound spinal rod includes a coupling which is adapted to be fixed to a bone anchor or dynamic bone anchor. The coupling is connected by a pivoting joint to a rod which is adapted to be connected to a bone anchor on an adjacent vertebra. The pivoting joint permits the spinal rod to pivot about an axis perpendicular to the longitudinal axis of the spinal rod.

Embodiments of the present invention include a dynamic spinal rod which provides load sharing while preserving range of motion and reducing stress exerted upon the bone anchors and spinal anatomy. The rod of the dynamic spinal rod is inserted in the first channel of the rod connector. The second channel of the rod connector is adapted to receive a vertical rod such that the rod connector can adjustable secure the dynamic spinal rod to the vertical rod. The dynamic spinal rod includes a rod-end which includes a ball-joint adapted to be fixed to a bone anchor or a dynamic bone anchor. The ball joint permits the coupling to be positioned such that rod is oriented in a preferred orientation relative to the bone anchor or dynamic bone anchor.

Embodiments of the present invention include an assembly comprising a bone anchor, and deflectable post assembled with a compound/dynamic spinal rod and a rod connector. The assembly provides load sharing while preserving range of motion and reducing stress exerted upon the bone anchors and spinal anatomy. The deflectable post is connected to a bone anchor by a ball-joint which permits the deflectable post to pivot and rotate relative the bone anchor. The compound/dynamic spinal rod is fixed to the deflectable post. The rod of the compound/dynamic spinal rod is inserted in the first channel of the rod connector. The second channel of the rod connector is adapted to receive a vertical rod such that the rod connector can adjustable secure the compound/dynamic spinal rod to a vertical rod. The assembly permits movement of adjacent vertebrae in a manner closely approximately the natural kinematics of the spine.

Common reference numerals are used to indicate like elements throughout the drawings and detailed description; therefore, reference numerals used in a drawing may or may not be referenced in the detailed description specific to such drawing if the associated element is described elsewhere. The first digit in a three digit reference numeral indicates the series of figures in which the referenced item first appears. Likewise the first two digits in a four digit reference numeral.

The terms "vertical" and "horizontal" are used throughout the detailed description to describe general orientation of structures relative to the spine of a human patient that is standing. This application also uses the terms proximal and distal in the conventional manner when describing the components of the spinal implant system. Thus, proximal refers to the end or side of a device or component closest to the hand operating the device, whereas distal refers to the end or side of a device furthest from the hand operating the device. For example, the tip of a bone screw that enters a bone would conventionally be called the distal end (it is furthest from the surgeon) while the head of the screw would be termed the proximal end (it is closest to the surgeon).

Rod Connectors

Figure 1B:
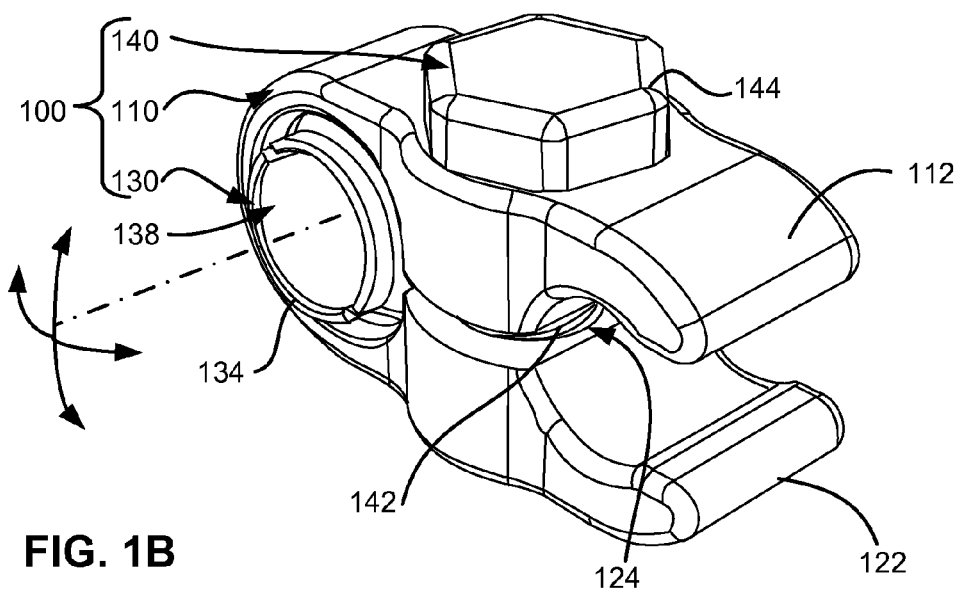
FIG. 1B shows a perspective view of the rod connector of FIG. 1A as assembled.
Figure 1C:
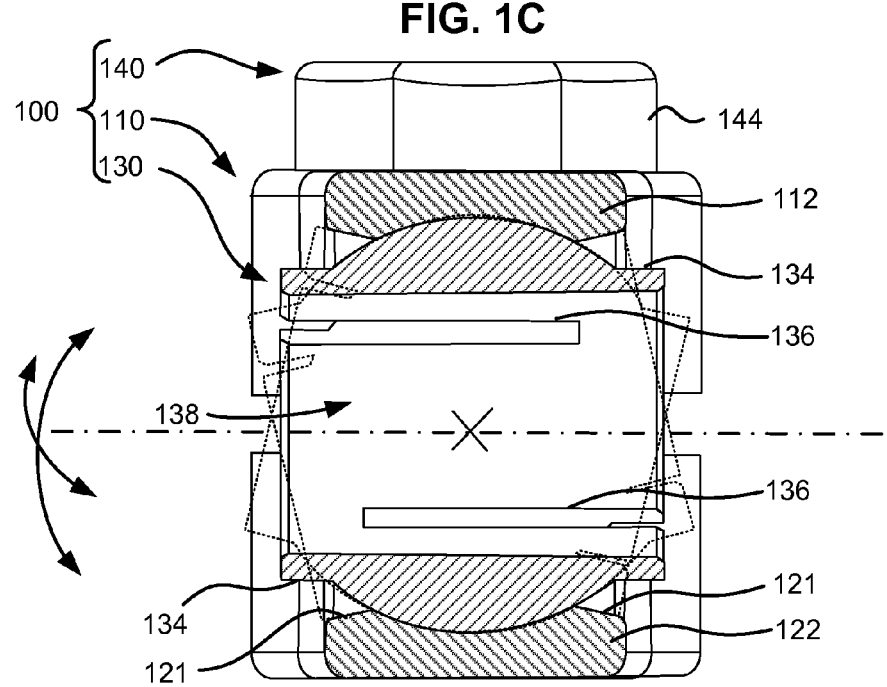
FIG. 1C shows a partial sectional view of the rod connector of FIG. 1A as assembled.
Figure 1D:
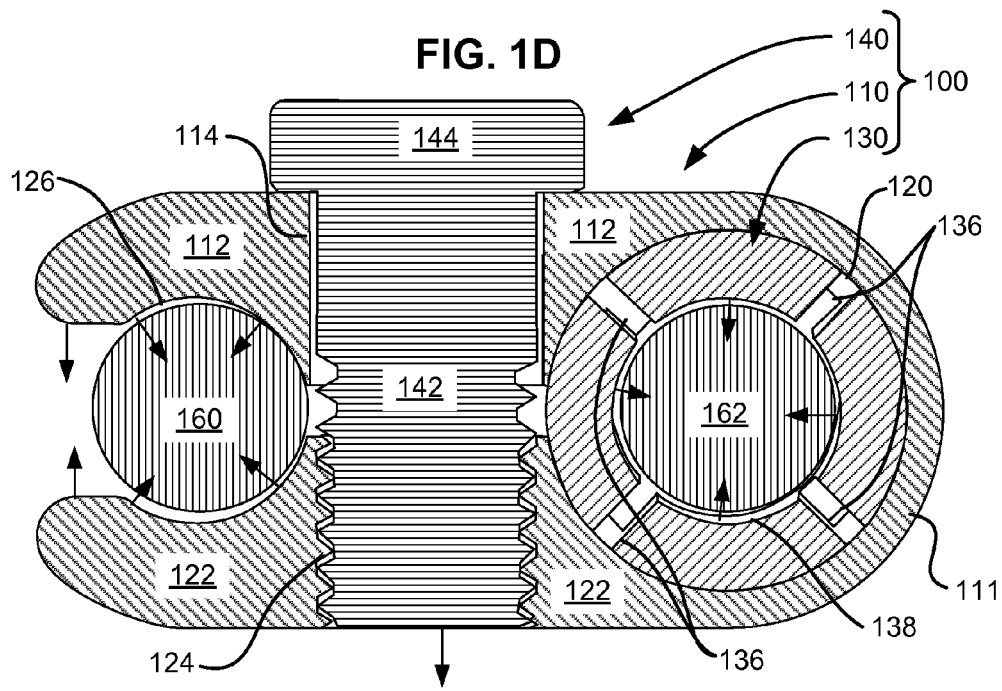
FIG. 1D shows a partial sectional view of the rod connector of FIG. 1A as assembled.
Figure 1E:
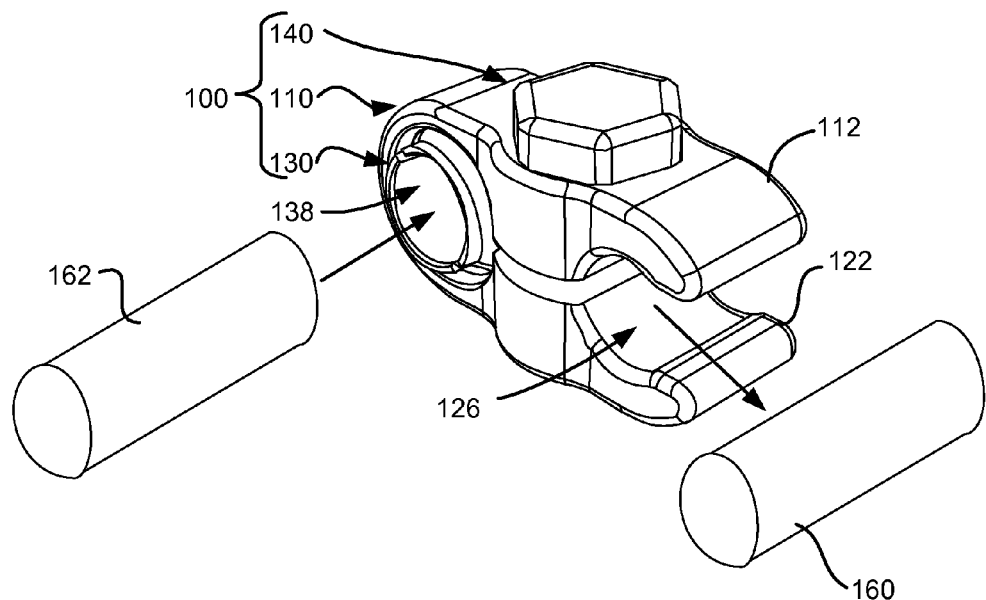
FIG. 1E illustrates the positioning of the rod connector of FIG. 1A relative to two spinal rods to be connected according to an embodiment of the invention.
Figure 1F:
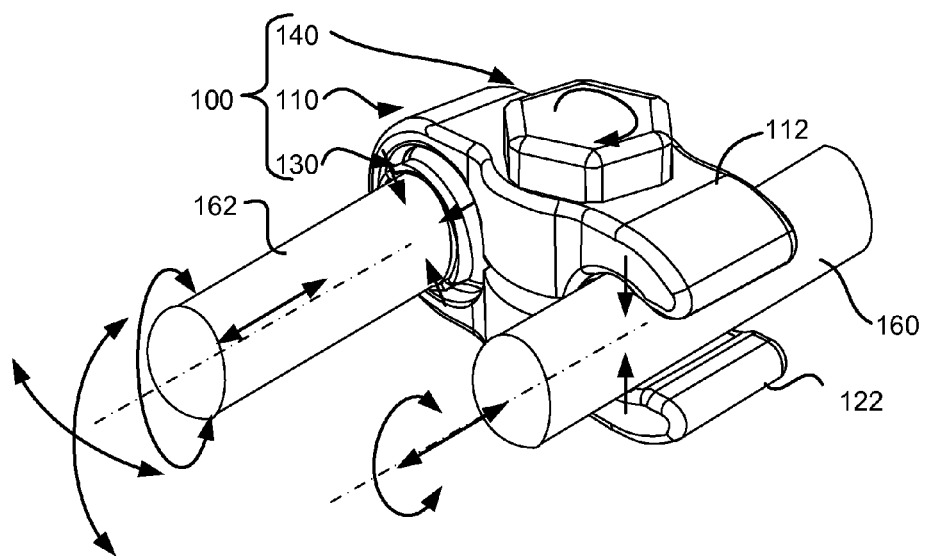
FIG. 1F illustrates the securing of the rod connector of FIG. 1A to connect two spinal rods according to an embodiment of the invention.

FIGS. 1A-1F show views of a rod connector 100 according to an embodiment of the invention. FIG. 1A shows an exploded view of the components of the rod connector 100. FIG. 1B shows a perspective view of the rod connector 100 as assembled. FIGS. 1C and 1D show two partial sectional views of the rod connector 100. FIGS. 1E and 1F illustrate the positioning and securing of the rod connector 100 relative to two spinal rods to be connected.

Referring first to FIG. 1A which shows an exploded view of the components of the rod connector 100. As shown in FIG. 1A rod connector 100 includes a housing 110, a compression ball 130 and a hex bolt or fastener 140. Housing 110 is generally U-shaped and is made up of an upper arm 112, a lower arm 122 connected by a curved wall 111. A smooth bore 114 passes through upper arm 112 and is in axial alignment with a threaded bore 124 which passes through lower arm 122. Hex bolt or fastener 140 includes a threaded shaft 142 sized to fit through smooth bore 114 and engage the threads of threaded bore 124. A hex head 144 of hex bolt or fastener 140 is adapted to be engaged by a wrench to tighten hex bolt or fastener 140 and thereby draw the upper arm 112 towards the lower arm 122.

Housing 110 includes a partially spherical socket 120 formed by curved surfaces of upper arm 112, lower arm 122 and curved wall 111. Socket 120 is open at both ends. Socket 120 has an angled rim 121 at each end. Socket 120 is sized to receive compression ball 130. Housing 110 also includes a cylindrical channel 126 formed by curved surfaces of upper arm 112 and lower arm 122. Channel 126 is open at each end and sized to receive a spinal rod. An opening between upper arm 112 and lower arm 122 allows a spinal rod to be pushed into channel 126.

Compression ball 130 includes a spherical section 132 and two lips 134, extending from spherical portion 132. Compression ball 130 incorporates four slots 136 which pass through the spherical section 132 and lips 134, and intersect a cylindrical ball channel 138. The four slots 136 are adapted to allow compression of compression ball 130. Cylindrical bore 138 is open at each end and sized, when uncompressed, to receive a spinal rod.

Referring now to FIG. 1B which shows a perspective view of the rod connector 100 as assembled. As shown in FIG. 1B, compression ball 130 is received into the spherical socket 120 of housing 110. Compression ball 130 is free to pivot and rotate within spherical socket 120. Contact between rims 134 and angled rims 121 operates to limit the range of pivoting motion of compression ball 130. Note that rims 121 are angled such that they approximately parallel to lips 134 upon contact. In a preferred embodiment, compression ball 130 can pivot 10 degrees in each direction (from the center position shown) prior to contact between rims 121 and lips 134. Thus in the preferred embodiment, total range of motion is 20 degrees in each axis and lips rims 121 are angled at 10 degrees relative to the central axis of socket 120. However larger or smaller ranges of motion can be selected as desired for the application by varying the dimensions and/or placement of rims 121 and lips 134.

Referring again to FIG. 1B hex bolt 140 is received in smooth bore 114 (not shown) and threaded bore 124. A hex head 144 of hex bolt 140 is adapted to be engaged by a wrench to tighten hex bolt 140 and thereby draw the upper arm 112 towards the lower arm 122.

Referring now to FIG. 1C which shows a partial sectional view of the rod connector 100 through the compression ball 130. As shown in FIG. 1C, spherical section 132 of compression ball 130 is received into the spherical socket 120 of housing 110 between upper arm 112 and lower arm 122. Compression ball 130 is free to pivot and rotate within spherical socket 120. Contact between lips 134 of compression ball 130 and angled rims 121 of housing 110 operates to limit the range of pivoting motion of compression ball 130. Note that rims 121 are angled such that they approximately parallel to lips 134 upon contact. In a preferred embodiment, compression ball 130 can pivot 10 degrees in each direction (from the center position shown) prior to contact between rims 121 and lips 134. Thus in the preferred embodiment total range of motion is 20 degrees in each axis and rims 121 are angled at 10 degrees relative to the central axis of socket 120. However larger or smaller ranges of motion can selected as desired for the application by varying the dimensions and/or placement of rims 121 and lips 134.

Referring now to FIG. 1D which shows a partial sectional view of the rod connector 100 through the compression ball 130 and cylindrical channel 126. Note that FIG. 1D, also shows, in section, two spinal rods 160, 162. Spinal rod 160 is received through cylindrical channel 126 on one side of housing 110. Spinal rod 162 is received through cylindrical bore 138 of compression ball 130 on the other side of housing 110. Note that, prior to tightening, spinal rod 162 can pivot and rotate relative to housing 110 in the same manner as compression ball 130. Spinal rod 162 can also slide and rotate within cylindrical bore 138 such that the position of housing 110 along and around the spinal rod 162 can be adjusted. Prior to tightening, spinal rod 160 can also slide within cylindrical channel 126 such that the position of housing 110 along the spinal rod 162 can be adjusted. Thus the relative position and angle of spinal rods 160 and 162 can be readily adjusted prior to tightening.

As, shown in FIG. 1D, the lower surface 145 of hex head 144 contacts upper arm 112 to draw it towards lower arm 122 upon tightening of threaded shaft 142 within threaded bore 124. As hex bolt 140 is tightened, upper arm 112 is drawn towards lower arm 122 compressing compression ball 130 around spinal rod 162. The diameter of cylindrical bore 138 is reduced as the size of slots 136 is diminished. The compression locks the position of compression ball 130 relative to housing 110 and locks the position of spinal rod 162 relative to compression ball 130. As hex bolt 140 is tightened, upper arm 112 is drawn towards lower arm 122 reducing the dimension of cylindrical channel 126. Upper arm 112 and lower arm 122 are forced into contact with spinal rod 160 compressing compression ball 130 around spinal rod 162 and locking the position of housing 110 relative to spinal rod 162. Thus the relative position and angle of spinal rods 160 and 162 is readily secured by tightening of hex bolt or fastener 140.

FIGS. 1E and 1F are a perspective view demonstrating how rod connector 100 can be secured to spinal rods 160 and 162. As shown in FIG. 1E, spinal rod 162 can be slid into cylindrical bore 138 of compression ball 130. Spinal rod 160 can either be slid into cylindrical channel 126 or inserted, sideways, through the gap between upper arm 112 and lower arm 122. Thus rod connector 100 can be applied either to the end or side of spinal rod 160. As shown in FIG. 1F, spinal rod 162 can be varied in angle and position relative to spinal rod 160 prior to tightening of hex bolt 140. Thus rod connector can secure spinal rod 162 to rod 160 at a position and angle suitable to the anatomy of the patient and the requirements of a spinal prosthesis of which rod connector 100 is a part.

Figure 2A:
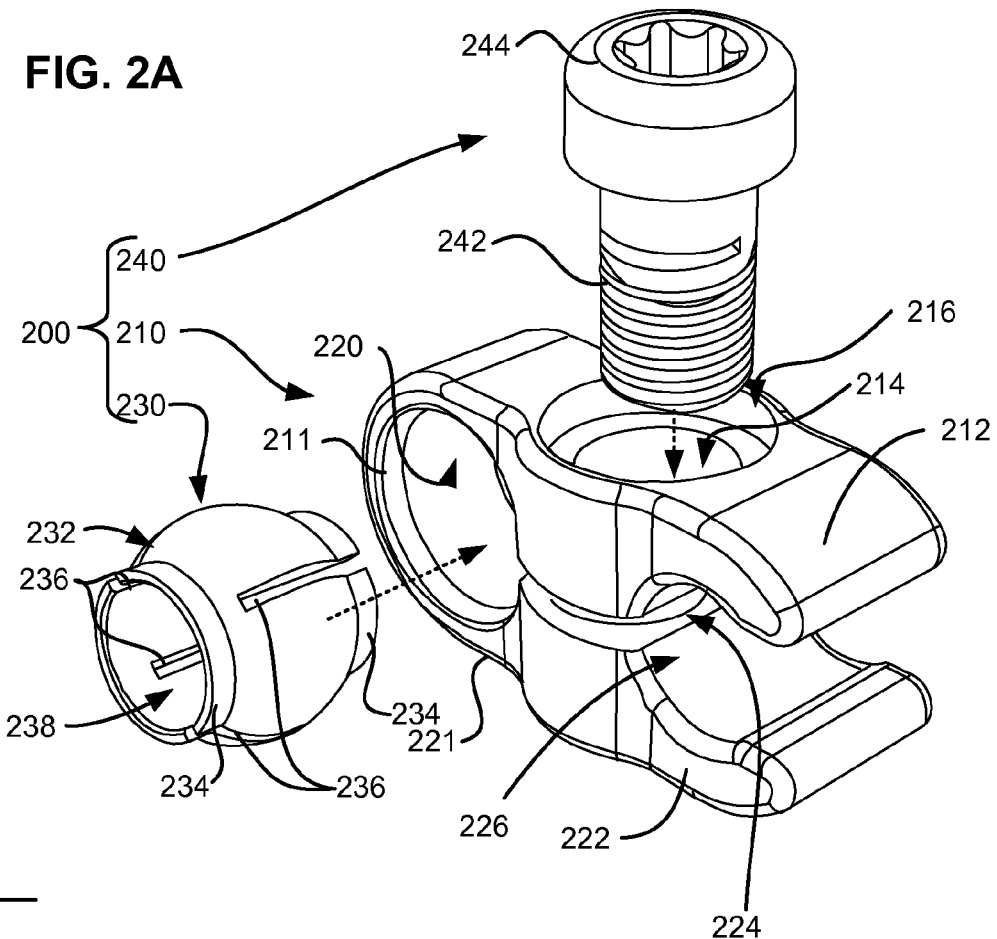
FIG. 2A shows an exploded view of a rod connector according to an embodiment of the invention.
Figure 2B:
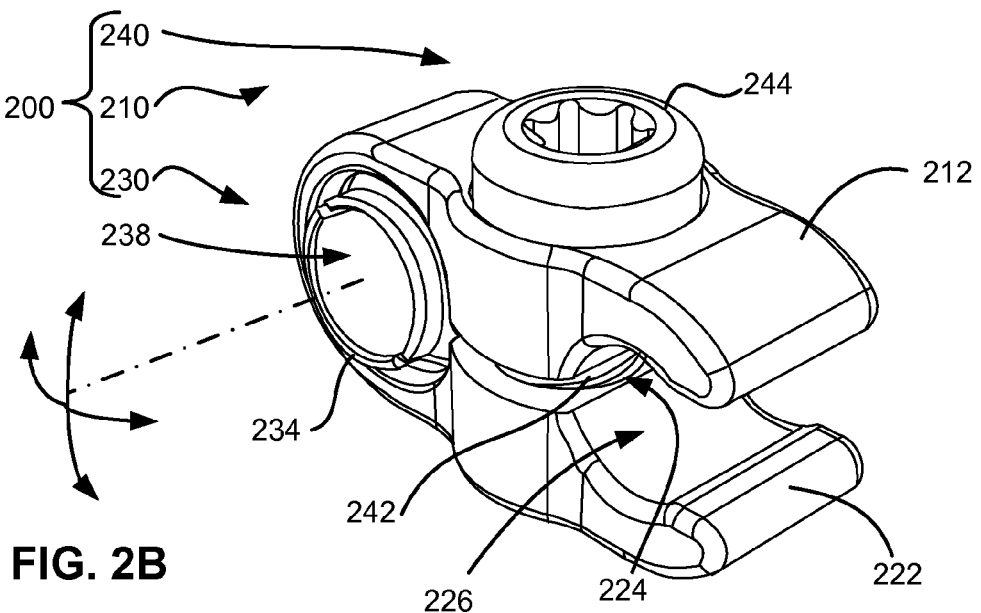
FIG. 2B shows a perspective view of the rod connector of FIG. 2A as assembled.
Figure 2C:
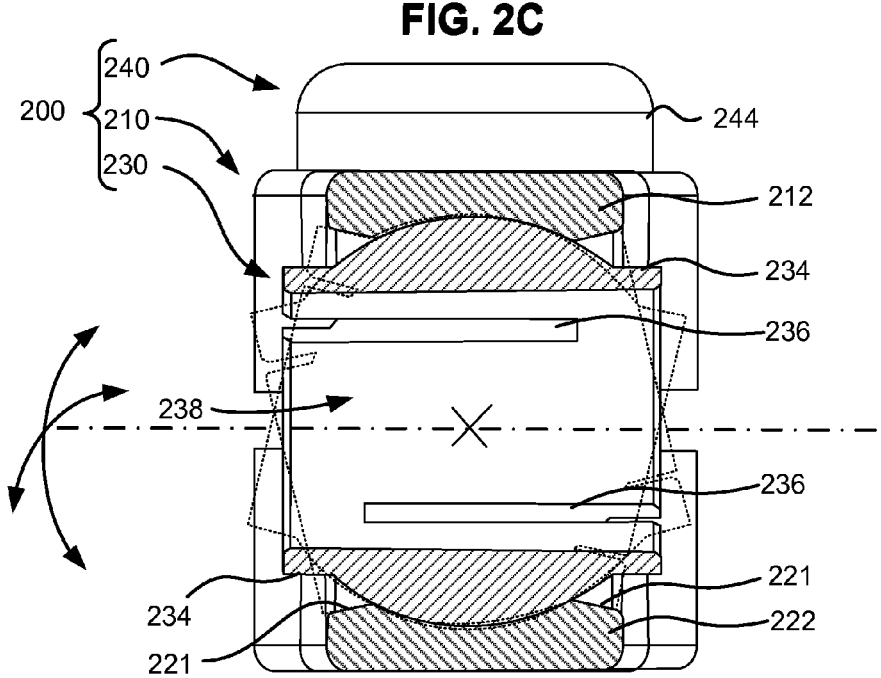
FIG. 2C shows a partial sectional view of the rod connector of FIG. 2A as assembled.
Figure 2D:
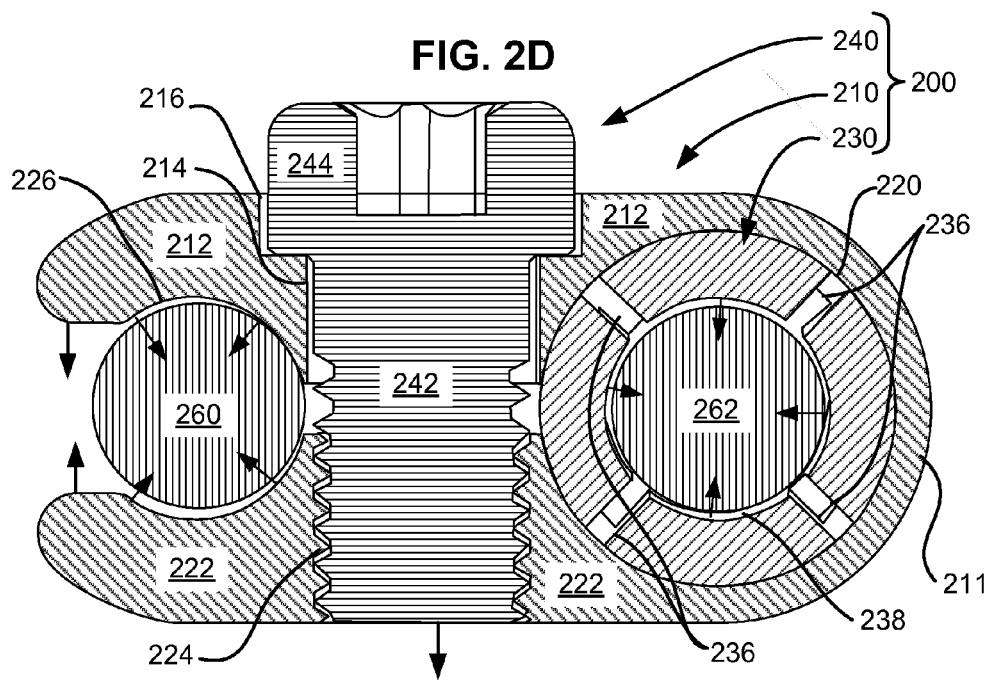
FIG. 2D shows a partial sectional view of the rod connector of FIG. 2A as assembled.

FIGS. 2A-2D show views of an alternative rod connector 200 according to an embodiment of the invention. FIG. 2A shows an exploded view of the components of the rod connector 200. FIG. 2B shows a perspective view of the rod connector 200 as assembled. FIGS. 2C and 2D show two partial sectional views of the rod connector 200.

Referring first to FIG. 2A which shows an exploded view of the components of the rod connector 200. As shown in FIG. 2A rod connector 200 includes a housing 210, a compression ball 230 and a bolt or fastener 240. Housing 210 is generally U-shaped and is made up of an upper arm 212, a lower arm 222 connected by a curved wall 211. A smooth bore 214 passes through upper arm 212 and is in axial alignment with a threaded bore 224 which passes through lower arm 222. Bolt or fastener 240 includes a threaded shaft 242 sized to fit through smooth bore 214 and engage the threads of threaded bore 224. A head 244 of bolt or fastener 240 includes a socket, such as a Torx socket or hex socket, adapted to be engaged by a wrench to tighten bolt 240 and thereby draw the upper arm 212 towards the lower arm 222. Note that upper arm 212 includes a counterbore 216 which at least partially receives head 244 of bolt 240 thereby reducing the profile of head 244.

Housing 210 includes a partially spherical socket 220 formed by curved surfaces of upper arm 212, lower arm 222 and curved wall 211. Socket 220 is open at both ends. Socket 220 has an angled rim 221 at each end. Socket 220 is sized to receive compression ball 230. Housing 210 also includes a cylindrical channel 226 formed by curved surfaces of upper arm 212 and lower arm 222. Channel 226 is open at each end and sized to receive a spinal rod. An opening between upper arm 212 and lower arm 222 allows a spinal rod to be pushed into channel 226.

Compression ball 230 includes a spherical section 232 and two lips 234, extending from spherical portion 232. Compression ball 230 incorporates four slots 236 which pass through the spherical section 232 and lips 234, and intersect a cylindrical ball channel 238. The four slots 236 are adapted to allow compression of compression ball 230. Cylindrical bore 238 is open at each end and sized, when uncompressed, to receive a spinal rod.

Referring now to FIG. 2B which shows a perspective view of the rod connector 200 as assembled. As shown in FIG. 2B, compression ball 230 is received into the spherical socket 220 of housing 210. Compression ball 230 is free to pivot and rotate within spherical socket 220. Contact between rims 234 and angled rims 221 operates to limit the range of pivoting motion of compression ball 230. Note that rims 221 are angled such that they approximately parallel to lips 234 upon contact. In a preferred embodiment, compression ball 230 can pivot 10 degrees in each direction (from the center position shown) prior to contact between rims 221 and lips 234. Thus in the preferred embodiment total range of motion is 20 degrees in each axis and lips rims 221 are angled at 10 degrees relative to the central axis of socket 220. However larger or smaller ranges of motion can selected as desired for the application by varying the dimensions and/or placement of rims 221 and lips 234.

Referring again to FIG. 2B bolt 240 is received in smooth bore 214 (not shown) and threaded bore 224. A head 244 of bolt 240 is adapted to be engaged by a wrench to tighten bolt 240 and thereby draw the upper arm 212 towards the lower arm 222.

Referring now to FIG. 2C which shows a partial sectional view of the rod connector 200 through the compression ball 230. As shown in FIG. 2C, spherical section 232 of compression ball 230 is received into the spherical socket 220 of housing 210 between upper arm 212 and lower arm 222. Compression ball 230 is free to pivot and rotate within spherical socket 220. Contact between lips 234 of compression ball 230 and angled rims 221 of housing 210 operates to limit the range of pivoting motion of compression ball 230. Note that rims 221 are angled such that they approximately parallel to lips 234 upon contact. In a preferred embodiment, compression ball 230 can pivot 10 degrees in each direction (from the center position shown) prior to contact between rims 221 and lips 234. Thus in the preferred embodiment total range of motion is 20 degrees in each axis and rims 221 are angled at 10 degrees relative to the central axis of socket 220. However larger or smaller ranges of motion can selected as desired for the application by varying the dimensions and/or placement of rims 221 and lips 234.

Referring now to FIG. 2D which shows a partial sectional view of the rod connector 200 through the compression ball 230 and cylindrical channel 226. Note that FIG. 2D, also shows, in section, two spinal rods 260, 262. Spinal rod 260 is received through cylindrical channel 226 on one side of housing 210. Spinal rod 262 is received through cylindrical bore 238 of compression ball 230 on the other side of housing 210. Note that, prior to tightening, spinal rod 262 can pivot and rotate relative to housing 210 in the same manner as compression ball 230. Spinal rod 262 can also slide and rotate within cylindrical bore 238 such that the position of housing 210 along and around the spinal rod 262 can be adjusted. Prior to tightening, spinal rod 260 can also slide within cylindrical channel 226 such that the position of housing 210 along the spinal rod 262 can be adjusted. Thus the relative position and angle of spinal rods 260 and 262 can be readily adjusted prior to tightening.

As shown in FIG. 2D, upper arm 212 includes a counterbore 216 which at least partially receives head 244 of bolt 240 thereby reducing the profile of head 244. As, shown in FIG. 2D, the lower surface 245 of head 244 contacts the bottom of counterbore 216 of upper arm 212 to draw it towards lower arm 222 upon tightening of threaded shaft 242 within threaded bore 224. As bolt 240 is tightened, upper arm 212 is drawn towards lower arm 222 compressing compression ball 230 around spinal rod 262. The diameter of cylindrical bore 238 is reduced as the size of slots 236 is diminished. The compression locks the position of compression ball 230 relative to housing 210 and locks the position of spinal rod 262 relative to compression ball 230. As bolt 240 is tightened, upper arm 212 is drawn towards lower arm 222 reducing the dimension of cylindrical channel 226. Upper arm 212 and lower arm 222 are forced into contact with spinal rod 260 compressing compression ball 230 around spinal rod 262 and locking the position of housing 210 relative to spinal rod 262. Thus the relative position and angle of spinal rods 260 and 262 is readily secured by tightening of bolt 240.

Figure 2E:
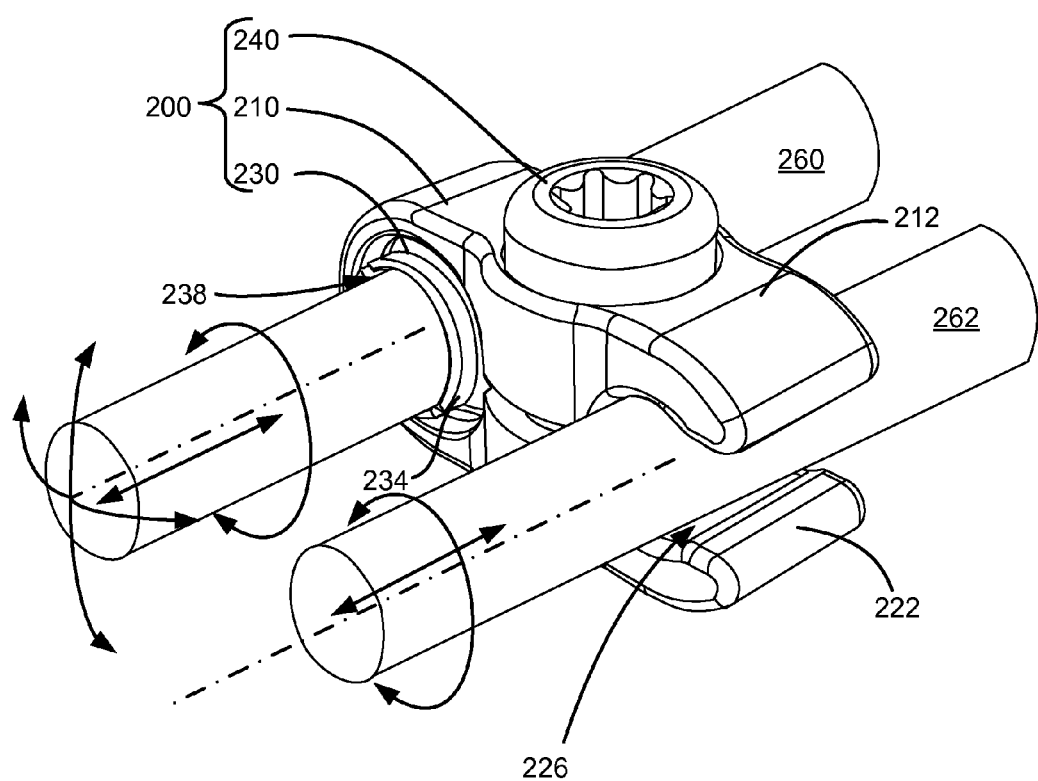
FIG. 2E illustrates the securing of the rod connector of FIG. 2A to connect two spinal rods according to an embodiment of the invention.

Rod connector 200 can be secured to spinal rods 260 and 262 in the same manner as shown in FIGS. 1E and 1F. FIG. 2E, shows rod connector 200 in combination with two spinal rods 260, 262. As shown in FIG. 2E, spinal rod 260 is received in cylindrical bore 238 of compression ball 230 whereas spinal rod 262 is received in cylindrical channel 226. Prior to tightening, spinal rod 262 can slide and rotate in cylindrical channel 226. Prior to tightening, spinal rod 260 can slide and rotate in cylindrical bore 238. Moreover, compression ball can all pivot relative to housing 210 thus allowing spinal rod 260 to also pivot relative to spinal rod 260. Thus, spinal rod 260 and 262 can be connected parallel to one another or at an angle to each other. The maximum angle between the spinal rods is determined by the configuration of compression ball 230 and housing 210 as previously described. In a preferred embodiment, the spinal rods can be connected of an angle of up to ten degrees from parallel with each other in any direction. In alternative configurations the spinal rods can be connected of an angle of up to 12, 15, 20, or 22.5 degrees from parallel with each other in any direction.

FIG. 3A illustrates a subassembly 300 of a spinal prosthesis utilizing the spinal rod connector 100 of FIG. 1A according to an embodiment of the invention. As shown in FIG. 3A, rod connector 100 can be used in conjunction with a spinal rod 302. Rod connector 100 can be used to connect one end of the spinal rod 302 to another spinal rod (not shown) at an adjustable angle while the other end of spinal rod 302 is mountable to a bone anchor (not shown). Suitable spinal rods 302 include, for example, conventional spinal rods or the spinal rods illustrated in FIGS. 5A-5C and 7A-7C. Rod connector 100 allows for connection of spinal subassembly 300 including spinal rod 302 to another spinal rod at a variety of relative positions and angles in order to form a spinal prosthesis either during an initial procedure or during revision surgery.

FIG. 3B illustrates another subassembly 310 of a spinal prosthesis utilizing the spinal rod connector 100 of FIG. 1A according to an embodiment of the invention. As shown in FIG. 3B, rod connector 100 can be used in conjunction with a spinal rod 302 and a bone anchor 312. Rod connector 100 can be used to connect one end of the spinal rod 302 to another spinal rod (not shown) at an adjustable angle while the other end of spinal rod 302 is mounted to bone anchor 312. Suitable bone anchors 312 include, for example, conventional pedicle screws or the bone anchors illustrated in FIGS. 4A-4D and 8A-8E. Rod connector 100 allows for connection of subassembly 310 to another spinal rod at a variety of relative positions and angles in order to from a spinal prosthesis either during an initial procedure or during revision surgery.

Figure 3C:
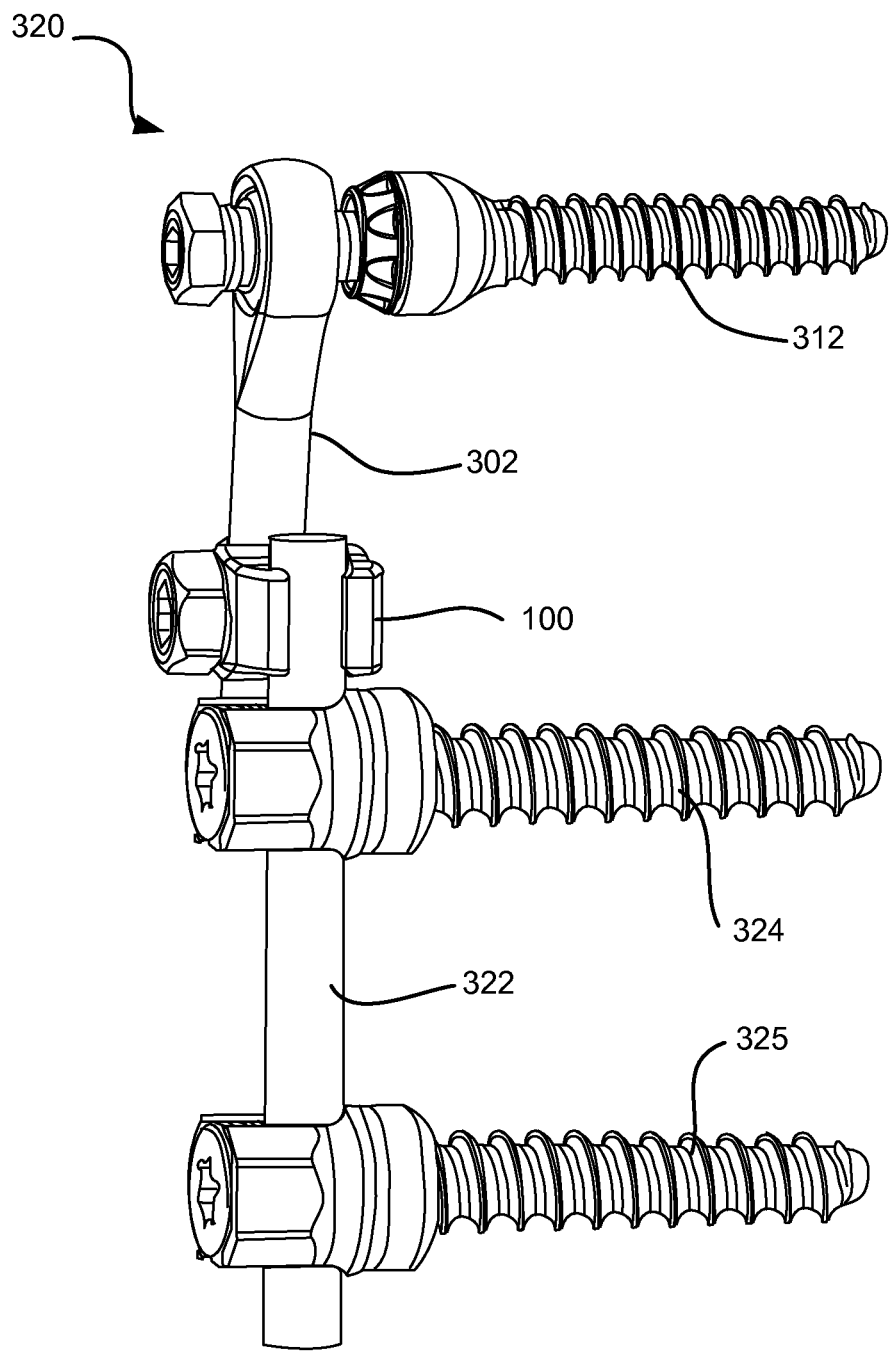
FIG. 3C illustrates a spinal prosthesis utilizing the spinal rod connector of FIG. 1A according to an embodiment of the invention.

FIG. 3C illustrates a spinal prosthesis 320 which can be utilized on one side of the spine to stabilize two adjacent spinal segments. Typically two such spinal prostheses will be used, one on each side of the spine. As shown in FIG. 3C, as spinal rod 322 is fastened between two pedicle screws 324, 325. Pedicle screws 324, 325 are typically implanted in the pedicles of adjacent vertebrae not shown. The combination of spinal rod 322 and pedicle screws 324, 325 fixes the relative position of the two vertebrae thus supporting the spine but preventing the movement of the vertebra. Such a construct can be used in conjunction with fusion of the vertebrae. As shown in FIG. 3C, rod connector 100 can be utilized to connect spinal/vertical rod 302 to spinal rod 322 in order to connect bone anchor 312 to spinal rod 322. Rod connector 100 allows spinal/vertical rod 302 to be connected to spinal rod 322 at a range of positions and angles suitable for the anatomy of the patient thereby facilitating construction and implantation of the prosthesis. Moreover, rod connector 100 allows for a revision procedure in which spinal/vertical rod 302 is connected to a spinal rod 322 implanted in a previous procedure.

FIG. 3D illustrates a posterior view of spinal prosthesis 320 implanted in a spine 340. As shown in FIG. 3D bone anchor 312 and pedicle screws 324, 325 are implanted in pedicles of vertebra 341, 342 and 343. Spinal rod 322 connects 324, 325 fixing the relative position of vertebrae 324 and 343. Rod connector 100 has been used to connect spinal rod 302 to spinal rod 322 at a position and angle that allows spinal rod 302 to be mounted to bone anchor 312 in order to complete the spinal prosthesis. Note that a second spinal prosthesis 330 is implanted on the contralateral side of the spine. In a preferred embodiment spinal rod 302 and bone anchor 312 provide for dynamic stabilization of vertebra 341 relative to vertebrae 342 and 343, supporting vertebra 341 while still providing for movement of vertebra 341. This allows for supporting a spinal motion segment adjacent a spinal fusion segment thereby preventing and/or reducing the accelerated degradation often seen at spinal segments adjacent a spinal fusion.

Bone Anchor And Compound Spinal Rod

FIGS. 4A-5D illustrate a bone anchor and a compound spinal rod which cooperate to support a vertebra while allowing for movement of a vertebra. FIGS. 4A-4C illustrate a preferred embodiment of a bone anchor 400. FIG. 4D illustrates a cannulated variant of the bone anchor of FIGS. 4A-4C. FIGS. 5A-5D illustrate a preferred embodiment of a compound spinal rod 500. The bone anchor and compound spinal rod can be utilized in conjunction with the rod connectors described above to create a spinal prosthesis or subassembly thereof as shown, for example, in FIGS. 3A-3D.

FIG. 4A shows an exploded view of bone anchor 400. FIG. 4B shows a perspective view of bone anchor 400, as assembled. FIG. 4C shows a sectional view of bone anchor 400. Referring first to FIG. 4A, bone anchor 400 includes, in this embodiment, three components: bone screw 420, deflectable post 440, and cap 410. Bone screw 420 comprises a threaded shaft 422 with a housing 430 at one end. Housing 430 may in some embodiments be cylindrical as previously described and is in some embodiments provided with splines/flutes. Housing 430 is preferably formed in one piece with threaded shaft 422. Housing 430 has a cavity 432 oriented along the axis of threaded shaft 422. Cavity 422 is open at the proximal end of housing 430 and is configured to receive deflectable post 440.

In a preferred embodiment, deflectable post 440 is a titanium post 5 mm in diameter. Deflectable post 440 has a retainer 442 at one end. At the other end of deflectable post 440 is a mount 444. Retainer 442 is a ball-shaped or spherical structure in order to form part of a linkage connecting deflectable post 440 to bone screw 420. Mount 444 is a low profile mount configured to connect deflectable post 440 to a vertical rod component (not shown, but see, e.g. FIGS. 5A-5C). Mount 444 comprises a threaded cylinder 446 to which the vertical rod component may be secured. Mount 444 in some embodiments also comprises a polygonal section 445 to prevent rotation of a component relative to mount 444.

Mount 444 includes a male hex extension 448 which may be engaged by a tool to hold stationary mount 444 during attachment to a vertical rod. At the proximal end of male hex extension 448 is a nipple 449 for securing male hex extension 448 into a tool. Hex extension 448 is breakaway component. Between hex extension 448 and threaded cylinder 446 is a groove 447. Groove 447 reduces the diameter of deflectable post 440 such that hex extension 448 breaks away from threaded cylinder 446 when a desired level of torque is reached during attachment of a vertical rod. The breakaway torque is determined by the diameter of remaining material and the material properties. In a preferred embodiment the breakaway torque is approximately 30 foot pounds. Thus, hex extension 448 breaks away during implantation and is removed. Nipple 449 is engaged by the tool in order to remove hex extension 448. Deflectable post 440 is also provided with flats 443 immediately adjacent mount 444. Flats 417 allow deflectable post 440 to be engaged by a tool after hex extension 448 has been removed.

Referring again to FIG. 4A, a cap 410 is designed to perform multiple functions including securing retainer 442 in cavity 432 of bone anchor 420. Cap 410 has a central aperture 412 for receiving deflectable post 440. In the embodiment of FIG. 4A, cap 410 has surface features 414, for example splines or flutes, adapted for engagement by an implantation tool or mounting a component, e.g. an offset connector. Surface features 414 may be, for example, engaged by a driver that mates with surface features 414 for implanting bone anchor 400 in a bone. As shown in FIG. 4A, cap 410 comprises a cylindrical shield section 418 connected to a collar section 416. Shield section 418 is designed to mate with cavity 432 of housing 430. Shield section 418 is threaded adjacent collar section 416 in order to engage threads at the proximal end of cavity 432 of housing 430. The distal end of shield section 418 comprises a flange 419 for securing retainer 442 within cavity 432 of housing 430.

Bone anchor 400 is assembled prior to implantation in a patient. FIG. 4B shows a perspective view of bone anchor 400 as assembled. When assembled, deflectable post 440 is positioned through cap 410. Cap 410 is then secured to the threaded end of cavity 432 (see FIGS. 4A and 4C) of housing 430 of bone anchor 420. Cap 410 has surface features 414 for engagement by a wrench to allow cap 410 to be tightened to housing 430. For example, cap 410 may be hexagonal or octagonal in shape or may have splines and/or flutes and/or other registration elements. Cap 410 may alternatively or additionally be laser welded to housing 430 after installation. Cap 410 secures deflectable post 440 within cavity 432 of bone anchor 420. Deflectable post 440 extends out of housing 430 and cap 410 such that mount 444 is accessible for connection to a vertical rod. Bone anchor 400 is implanted in a bone in the configuration shown in FIG. 4B and prior to attachment of a vertical rod or other spinal rod. A special tool may be used to engage the surface features 414 of cap 410 during implantation of bone anchor 400 into a bone.

FIG. 4C shows a sectional view of a bone anchor 400. Retainer 442 fits into a hemispherical pocket 439 in the bottom of cavity 432 of housing 430. The bottom edge of cap 410 includes the curved flange 419 which secures ball-shaped retainer 442 within hemispherical pocket 439 while allowing ball-shaped retainer 442 to pivot and rotate. Accordingly, in this embodiment, a ball-joint is formed. FIG. 4C also illustrates deflection of deflectable post 440—dashed lines. Applying a force to mount 444 causes deflection of deflectable post 440 of bone anchor 400. Deflectable post 440 pivots about a pivot point 403 indicated by an X. Deflectable post 440 may pivot about pivot point 403 in any direction, as shown by arrow 450. Concurrently or alternatively, deflectable post 440 can rotate, as shown by arrow 452, about the long axis of deflectable post 440 (which also passes through pivot point 403). In this embodiment, pivot point 403 is located at the center of ball-shaped retainer 442. In a preferred embodiment, deflectable post 440 may deflect from 0.5 mm to 2 mm in any direction before making contact with limit surface 413. More preferably, deflectable post 440 may deflect approximately 1 mm before making contact with limit surface 413. After a fixed amount of deflection, deflectable post 440 comes into contact with limit surface 413 of cap 410. Limit surface 413 is oriented such that when deflectable post 440 makes contact with limit surface 413, the contact is distributed over an area to reduce stress on deflectable post 440. In this embodiment, the deflectable post 440 contacts the entire sloping side of the conically-shaped limit surface 413. In another embodiment, the deflectable post may only contact a limit ring that is located distally from the flange 419 of cap 410. After deflectable post 440 comes into contact with limit surface 413, further deflection requires deformation (bending) of deflectable post 440.

FIG. 4D shows a sectional view of a bone anchor 400d which is a cannulated variant of bone anchor 400 of FIGS. 4A-4C. As shown, bone anchor 400d is essentially identical to bone anchor 400 with the addition of a first bore 460 which passes axially through deflectable post 440 and second bore 462 which passes axially through bone anchor 420 from the bottom of pocket 439 to the distal tip of bone screw 420. As shown in FIG. 4D, bone anchor 440d may optionally include one or more side holes 464 which pass through bone screw 420 and communicates with second bore 462. Where the first bore 460 of the deflectable post 440 communicates with the second bore 462 of the bone screw 420, the bores 460, 462 can be fluted or broadened out so that they communicate even when the deflection post 440 and the bone screw 420 are not in alignment. Accordingly, this embodiment includes a cannulated bone anchor such that a cannula is defined by the bone anchor through the deflectable post 440 and through the bone screw 420 such that a needle can be inserted through the bone anchor to delivery a medication, a bone cement and/or monitor the bone that the bone anchor is inserted into. Optional side holes 464 serve as ports for the emission of bone cement and/or medication.

As shown in FIG. 4D, after assembly, first bore 460 and second bore 462, are aligned to form a continuous channel which passes through the entire length of bone anchor 400d. A guidewire or needle can be inserted through the continuous channel (made up of first bore 460 and second bore 462) which passes through the entire length of bone anchor 400e in order to guide insertion of the bone anchor. Additionally, a cannulated bone anchor can be introduced into a patient over a guidewire. Once a guidewire is inserted to a desired location, the cannulated bone anchor can be introduced over the guidewire to the desired location. Using a guidewire is particularly useful during percutaneous introduction of a bone anchor where the target location of the bone anchor cannot be directly visualized. The guidewire can be, for example a k-wire or other guidewire used in orthopedic surgery to facilitate the positioning of bone anchors. Further, the cannulated bone anchor can provide a port or tube for the ingrowth of bone. Further, the cannulated bone anchor can have a plurality of openings 464 in the bone screw that can preferably communicate with the central bores for enhanced bone ingrowth.

Figure 5A:
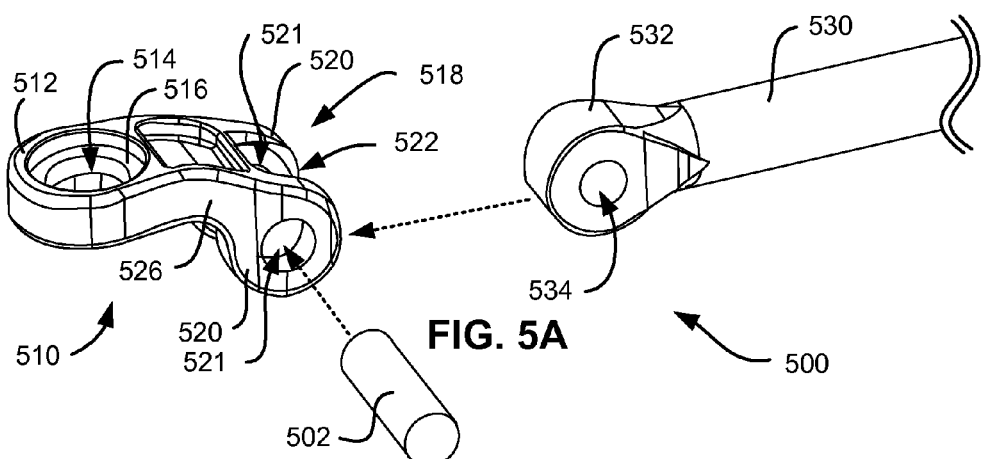
FIG. 5A shows an exploded view of a compound spinal rod suitable for use with the rod connectors of FIGS. 1A and 2A according to embodiments of the invention.
Figure 5B:
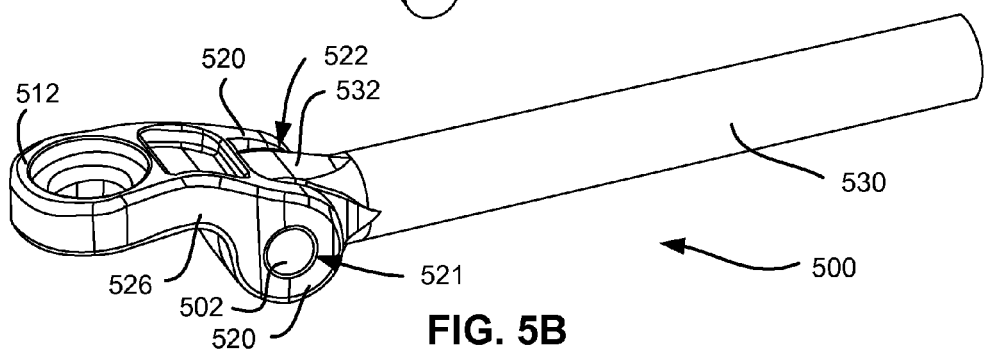
FIG. 5B shows a perspective view of the compound spinal rod of FIG. 5A as assembled.
Figure 5C:
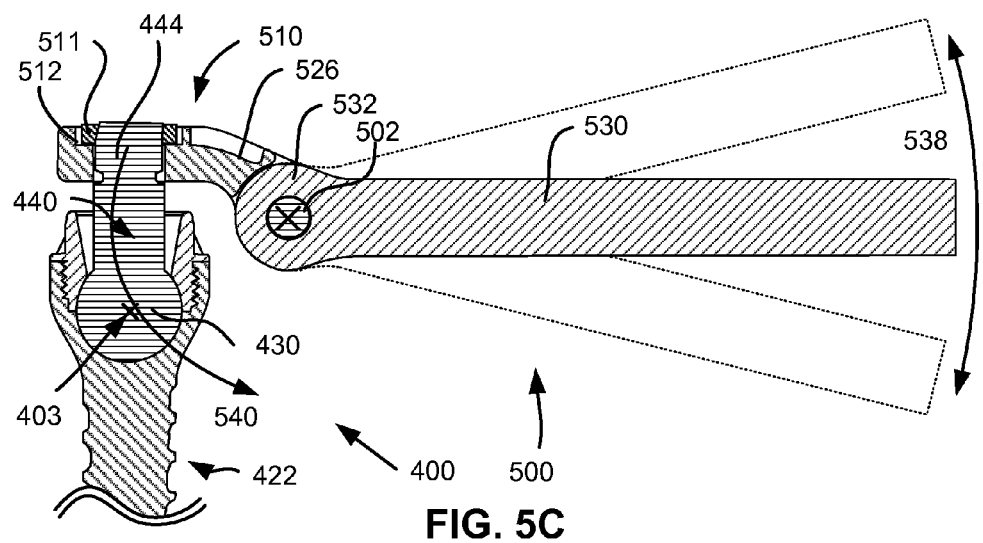
FIG. 5C shows a sectional view of the compound spinal rod of FIG. 5A as assembled.

FIGS. 5A-5C show exploded, perspective, and sectional views of an embodiment of a compound spinal/vertical rod. Referring first to FIG. 5A, compound rod 500 includes a coupling 510 joined by a pin 502 to a rod 530. As shown in FIG. 5A, coupling 510 has a mount 512 at one end and a clevis 518 at the other end. Mount 512 is configured to be secured to a bone anchor. Mount 512 includes a bore 514 therethrough sized to receive the mount of a bone anchor (see e.g. mount 444 of FIGS. 4A and 4B). Bore 514 is in some embodiments configured to mate with the mount of a bone anchor to preclude rotation—for example by being polygonal in section. However, in alternative embodiments, bore 514 is circular in section. Coupling 510 is adapted to be secured to a bone anchor using, for example a threaded nut. Coupling 510 is, in some embodiments, provided with a recess 516 to reduce the profile of a nut above coupling 510.

Coupling 510 is connected to clevis 518 by offset or dogleg connector 526. The dogleg connector 526, in addition to the other components, provides for enhanced motion of a spinal prosthesis so that the prosthesis can model the natural kinetics of the spine (See, e.g. FIG. 5C). Clevis 518 has two arms 520 separated by a slot 522. Each arm 520 has an aperture 521 for receiving pin 502. Slot 522 is size to receive a disc 532 formed at one end of rod 530. Disc 532 also has an aperture 534 for receiving pin 502. Thus rod 530 may rotate relative to coupling 510 about the axis of rotation of pin 502. The axis of rotation of pin 502, in this embodiment, is substantially perpendicular to the axis of bore 514 except that the pin axis is offset from the bore axis.

FIG. 5B shows compound rod 500 as assembled. Compound rod 500 is assembled prior to implantation in a patient. Disc 532 is placed in slot 522 between arms 520. Aperture 534 is aligned with apertures 521. Pin 502 is then inserted between arms 520, across slot 522 and through aperture 534 thereby securing disc 532 within slot 522. Pin 502 can be secured mechanically or bonded to clevis 518 by e.g. laser welding.

FIG. 5C shows a sectional view of compound rod 500 as assembled and mounted to the mount 444 of bone anchor 400 of FIGS. 4A-4C. As shown in FIG. 5C mount 512 of coupling 510 is secured to mount 444 of deflectable post 440 by a nut 511. Coupling 510 is also joined by pin 502 to rod 530. Mount 512 of coupling 510 has a bore 514 for receiving the mount 444 of a bone anchor 400. After assembly, rod 530 is free to pivot relative to coupling 510 around the axis of pin 502 as shown by arrow 538. Further, it is noted that the pivot pin 502 and the pivot axis is located to the side of the housing 430 and substantially perpendicular to and offset from the longitudinal axis of the threaded shaft 422 of the bone anchor 400. Further, the pivot pin 502 is located below the level where the compound rod 500 is connected to the deflectable post 440 of the bone anchor 400. The mount 444 and pin 502 are approximately equidistant from pin 502 of compound rod 500 and pivot about pivot point 403. However, dogleg connector 526 changes the position of pin 502 relative to mount 444. The shape of the dogleg connector 526 controls the angle between the mount 444 and pivot point 403 relative to pin 502 and thus can be designed to modulate the direction of movement of pivot point 403. The length of the dogleg connector controls the distance between the pin 502 and pivot point 403 and thus can be designed to modulate the amount of movement of pivot point 403 for a given amount of deflection of coupling 510. The kinematics of pivot point 403 enabled by pin 502 and dogleg connector 526 permits a spinal prosthesis to more closely approximate the natural kinematics of the spine by coupling rotation or coupling 510 with translation of pivot point 403 as shown by arrow 540. Although compound rod 500 has been shown in combination with bone anchor 400 of FIGS. 4A-4C, compound rod 500 can, in other embodiments, be utilized with any other of the bone anchors described herein.

FIGS. 6A-6D illustrate another alternative bone anchor 600. FIG. 6A shows an exploded view of bone anchor 600. FIG. 6B shows a perspective view of bone anchor 600, as assembled. FIG. 6C shows a sectional view of bone anchor 600. FIG. 6D illustrates deflection of the deflectable post of bone anchor 600. Referring first to FIG. 6A, bone anchor 600 includes, in this embodiment, four components: bone screw 620, deflectable post 640, centering rod 660, and cap 610. Bone screw 620 comprises a threaded shaft 622 with a housing 630 at one end. Housing 630 is provided with tool engagement features 636 which are adapted to be engaged by a wrench (not shown) to drive threaded shaft 622 into a bone. Housing 630 is preferably formed in one piece with threaded shaft 622. Housing 630 has a cavity 632 oriented along the axis of threaded shaft 622. Cavity 632 is open at the proximal end of housing 630 and is configured to receive deflectable post 640.

Centering rod 660 is a cylindrical rod having a metal core 661 covered with a tubular polymer sleeve 663. In a preferred embodiment, core 661 is made of a superelastic metal—for example Nitinol. In one embodiment, core 661 is a superelastic Nitinol wire having a diameter between 0.060 and 0.080 inches. In an exemplary embodiment, core 661 is a superelastic nitinol wire having a diameter of 0.063 inches. In a preferred embodiment sleeve 663 is made of a wear-resistant biocompatible polymer—for example PEEK.

The proximal end 662 of centering rod 660 is sized and configured to be received within deflectable post 640. The distal end 664 of centering rod 660 is sized and configured to be received within bone screw 620. In a preferred embodiment both ends of centering rod 660 are cylindrical in shape. However, in alternative embodiments, the proximal end 662 and distal end of rod 660 may have other than a circular section, for example, square, oval, rectangular, or other polygonal. Note that the distal end 664 and proximal end 662 of centering rod 660 can have the same, or different, sectional shapes.

The center section 666 of centering rod 660 is designed to bend in response to deflection of deflectable post 640 relative to bone screw 620 and exert a restorative centering force upon deflectable post 640. The restorative force tends to align the longitudinal axis of the deflectable post 640 with the longitudinal axis of the bone screw 620. The force increases as the angle between the deflectable post 640 and bone screw 620 increases. The diameter and shape of center section 666 of centering rod 660 can be designed/selected to achieve a desired restorative force for a given angle and/or direction of deflection. Also, the diameter of core 661 and thickness of sleeve 663 can be selected to achieve a desired restorative force. Center section 666 can be cylindrical but may have other than a circular section, for example, square, oval, rectangular, or other polygonal. The force/deflection response can accordingly be isotropic or anisotropic depending upon the shape of center section 666.

A hemispherical pocket 639 (shown by dashed lines) is formed in the bottom of cavity 632 of housing 630. A bore 634 (shown by dashed lines) extends distally from the bottom of hemispherical pocket 639 along the longitudinal axis of bone screw 620. Bore 634 is sized and configured to receive the distal end 664 of centering rod 660. Bore 634 is chamfered where it meets hemispherical pocket 639 to allow for bending of centering rod 660. In a preferred embodiment both centering rod 660 and bore 634 are cylindrical in shape such that the distal end 664 of centering rod 660 may rotate about its longitudinal axis within bore 634.

Deflectable post 640 can be made, for example, from cobalt chrome or titanium. In a preferred embodiment deflectable post 640 is between 4.5 and 6.5 mm in diameter and made in one piece from cobalt chrome. Deflectable post 640 has a retainer 642 at the distal end. Retainer 642 is a ball-shaped or spherical structure in order to form part of a linkage connecting deflectable post 640 to bone screw 620. At the proximal end of deflectable post 640 is a mount 644. Mount 644 is a low profile mount configured to connect deflectable post 640 to a vertical rod component (not shown). Mount 644 comprises a threaded section 646 to which the vertical rod component may be secured. Mount 644 has at the proximal end a socket 649 which can be engaged by a wrench during the securing of a vertical rod to mount 644.

A bore 670 (show by dashed lines) extends proximally from the bottom of ball-shaped retainer 642 along the longitudinal axis of deflectable post 640. Bore 670 includes a proximal bore 672 sized and configured to receive the proximal end 662 of centering rod 660. Bore 670 has a larger distal bore 676. Distal bore 676 is sized to allow bending of centering rod 660 and deflection of deflectable post 640. In some embodiments, distal bore 676 is sized such that center section 666 does not contact the sides of distal bore 676 over the full range of motion of deflectable post 640. In alternative embodiments, distal bore 676 is sized and shaped such that center section 666 comes into contact progressively with the sides of distal bore 676 over the range of motion of deflectable post 640 thereby modulating the centering force. The sleeve 663 protects the core 661 of centering rod 660 from wear during moving contact with distal bore 676. Distal bore 676 is chamfered where it intersects the surface of retainer 642. In a preferred embodiment both centering rod 660 and proximal bore 672 are cylindrical in shape such that the proximal end 662 of centering rod 660 may rotate about its longitudinal axis within proximal bore 672.

Referring again to FIG. 6A, a cap 610 is designed to perform multiple functions including securing retainer 642 in cavity 632 of bone screw 620. Cap 610 has a central aperture 612 for receiving deflectable post 640. As shown in FIG. 6A, cap 610 comprises a cylindrical shield section 618 connected to a collar section 616. Shield section 618 is designed to mate with cavity 632 of housing 630. The distal end of shield section 618 comprises a curved flange 619 for securing retainer 642 within cavity 632 of housing 630. Shield section 618 is threaded adjacent collar section 616 in order to engage threads at the proximal end of cavity 632 of housing 630. Cap 610 can be provided with surface features for engagement by a tool during attachment of cap 610 to housing 630 (such surface features can also be used to drive bone screw 620 into a bone). For example, cap 610 may be hexagonal or octagonal in shape or may have splines, sockets and/or flutes and/or other registration elements.

Bone anchor 600 is assembled prior to implantation in a patient. FIG. 6B shows a perspective view of bone anchor 600 as assembled. During assembly, centering rod 660 (shown by dashed lines) is received in bore 670 and bore 634 (see FIGS.

6A and 6C). Because bore 670 and bore 634 are closed, it is not necessary to fix centering rod 660 to either of deflectable post 640 or bone screw 620. However, if desired, centering rod 660 can be attached to either or both of deflectable post 640 or bone screw 620 by mechanical means (e.g. pins), welding or other fastening method/device. Retainer 642 (not shown) is received in hemispherical pocket 639 (not shown). Deflectable post 640 is then positioned through aperture 612 of cap 610. Cap 610 is then secured to the threaded end of cavity 632 (see FIGS. 6A and 6C) of housing 630 of bone screw 620. Cap 610 may alternatively or additionally be laser welded to housing 630 after installation. Cap 610 secures retainer 642 within cavity 632 of bone screw 620. Deflectable post 640 extends out of housing 630 and cap 610 such that mount 644 is accessible for connection to a vertical rod. Bone anchor 600 is typically implanted in a bone in the configuration shown in FIG. 6B and prior to attachment of a vertical rod or other spinal rod. A tool may be used to engage the surface features 636 of housing 630 during implantation of bone anchor 600 into a bone.

FIG. 6C shows a sectional view of a bone anchor 600 after assembly. Retainer 642 fits into a hemispherical pocket 639 in the bottom of cavity 632 of housing 630. The distal edge of cap 610 includes the curved flange 619 which secures ball-shaped retainer 642 within hemispherical pocket 639 while allowing ball-shaped retainer 642 to pivot and rotate. Accordingly, in this embodiment, a ball-joint is formed. Deflectable post 640 pivots about a pivot point 603 indicated by an X. In a preferred embodiment the pivot point 603 is positioned on the center of the section of centering rod 660 (at least when the longitudinal axis of the deflectable post 640 and bone screw 620 are aligned). Deflectable post 640 may pivot about pivot point 603 in any direction, as shown by arrow 650. Concurrently or alternatively, deflectable post 640 can rotate, as shown by arrow 652, about the long axis of deflectable post 640 (which also passes through pivot point 603).

As shown in FIG. 6C, distal end 664 of centering rod 660 is received within bore 634 of bone screw 620. Proximal end 662 of centering rod 660 is received within proximal bore 672 of deflectable post 640. Center section 666 of centering rod 660 is received within distal bore 676 of deflectable post 640. Note that an annular cavity 674 exists around center section 666 leaving center section 666 free to flex when deflectable post 640 pivots about pivot point 603.

Where flexible components are incorporated in a spinal device, one important consideration is the possibility of ineffectiveness of the flexible element during the life of the device. One advantage of the present design of bone anchor 600 is that the centering rod 660 is not relied upon for securing mount 644 to bone screw 620. Thus, if centering rod 660 becomes ineffective at some point, mount 644 and any spinal components connected to it remain attached to bone screw 620. Thus it is an advantage of the present design of bone anchor 600 that, the "flexible element" of this design is operable even if it should become ineffective with respect to centering.

It is also advantageous that, in the present design centering rod 660 is fully enclosed within bore 670 and bore 634. Thus, where core 661 is Nitinol and sheath 663 is PEEK, the Nitinol and PEEK are not in direct contact with tissues of the body. Furthermore, even if centering rod 660 becomes ineffective, no parts of centering rod 660 can migrate past ball 642 into the tissues surrounding bone anchor 600. Thus it is an advantage of the present design of bone anchor 600 that the flexible Nitinol/PEEK element is entirely enclosed within the device and not exposed to contact with tissues.

FIG. 6D shows a sectional view of bone anchor 600 and illustrates deflection of deflectable post 640. Applying a force to mount 644 causes deflection of deflectable post 640 of bone anchor 600. Deflectable post 640 pivots about pivot point 603 located at the center of ball-shaped retainer 642. Proximal end 662 of centering rod 660 remains aligned with deflectable post 640 whereas distal end 664 remains aligned with bone screw 620. Thus center section 666 of centering rod 660 bends elastically in response to deflection of deflectable post 640. Centering rod 660 thus applies a resilient restorative force upon deflectable post 640 pushing it back into alignment with bone screw 620. The magnitude of the force increases as the deflection increases. The magnitude of the force can be selected based on the configuration and material of centering rod 660. For example a larger diameter cylindrical nitinol rod core 661 will provide a larger centering force than a smaller diameter rod for the same amount of deflection. In a preferred embodiments centering rod 660 is floating, that is to say that it is not fixed to one or both of deflectable post 640 and bone screw 620. Thus, upon deflection of deflectable post 640, centering rod 660 can slide somewhat in one or both of proximal bore 672 and bore 634 such that the centering rod 660 is not placed under longitudinal tension during deflection of deflectable post 640.

In a preferred embodiment, deflectable post 640 may deflect from 0.5 mm to 2 mm in any direction before making contact with limit surface 613. More preferably, deflectable post 640 may deflect approximately 1 mm before making contact with limit surface 613. After a fixed amount of deflection, deflectable post 640 comes into contact with limit surface 613 of cap 610. Limit surface 613 is oriented such that when deflectable post 640 makes contact with limit surface 613, the contact is distributed over an area to reduce stress on deflectable post 640. In this embodiment, the deflectable post 640 contacts the entire sloping side of the conically-shaped limit surface 613. After deflectable post 640 comes into contact with limit surface 613, further deflection requires deformation (bending) of deflectable post 640. Bending of deflectable post 640 requires significantly more force than bending of centering rod 660.

As previously stated, the deflection/force response of a centering rod (and a ball-joint incorporating such a centering rod) can be customized based on the choice of design, dimensions and materials. It is contemplated, for example, that the deflection rod can be made in stiffness that can replicate a 70% range of motion and flexibility of the natural intact spine, a 50% range of motion and flexibility of the natural intact spine and a 30% range of motion and flexibility of the natural intact spine for providing in a kit for a doctor to use. After a selected amount of deflection a deflectable post (see e.g. deflectable post 640 of FIGS. 6A-6D) will make contact with a limit surface (for example 1 mm of deflection. Further deflection then requires bending of the deflectable post 640. The deflectable post 640 therefore responds more stiffly as the load increases. As the deflection increases, the stiffness of the deflectable post 640 to further deflection is increased such that the force required per unit of additional deflection increases in response to the load placed on the spine and deflection rod.

Initially, as load or force is first applied to the deflectable post by the spine, the deflection of the deflectable post rod responds about linearly to the increase in the load. After the post makes contact with the limit surface, the deflectable post responds more stiffly. In this region, a greater amount of load or force needs to be placed on the deflectable post in order to obtain the same amount of deflection that was realized prior to this point. Accordingly, the deflectable post of this example provides a range of motion where the load supported increases about linearly as the deflection increases and then with increased deflection the load supported increases more rapidly in a non-linear manner. The transition from lower stiffness to higher stiffness region depends upon the distance between the deflectable post and the limit surface of the cap. This distance may be customized as previously described so that the transition occurs after the desired amount of deflection, for example after about 1 mm of deflection or after about 2 mm of deflection.

As shown, in the embodiment of FIG. 6D, sheath 663 of centering rod 660 makes contact with the walls of distal bore 676 upon deflection of deflectable post 640. Sheath 663 thereby protects core 661 from wear during moving contact with the walls of distal bore 676. Furthermore, sheath 663, is in some embodiments compressed between core 661 and the walls of distal bore 676. Thus sheath 663 being resilient will modulate and contribute to the restorative force applied to deflectable post 640 by centering rod 660. The effect of sheath 663 can be adjusted by modifying the thickness and/or material of sheath 663. For example, PEEK of different durometers can be selected for sheath 663 thereby resulting in a different force/deflection response for deflectable post 640.

Figure 6E:
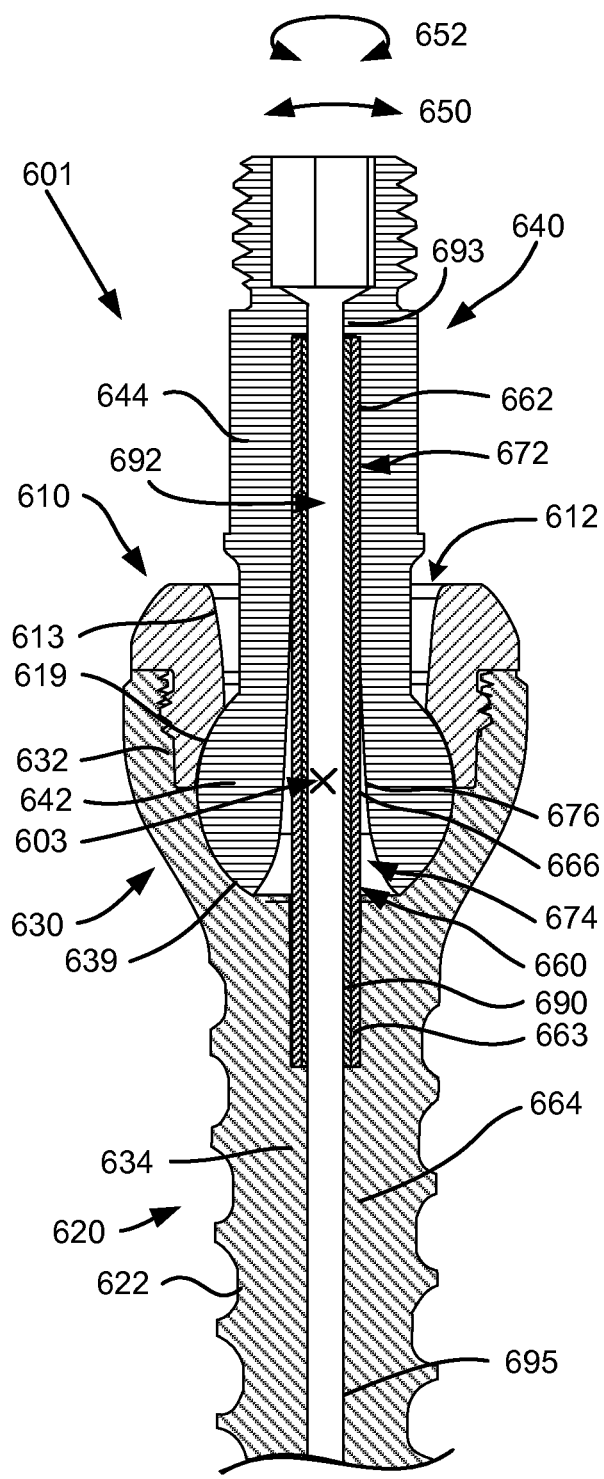
FIG. 6E shows a sectional view of a variant of the alternative dynamic bone anchor of FIG. 6A as assembled.

FIG. 6E shows a sectional view of a dynamic bone anchor 601 which is a variant of dynamic bone anchor 600 in which the bone anchor is cannulated. The elements of FIG. 6E that are similar to FIGS. 6A, 6B, 6C and 6D have similar reference numbers. Referring to FIG. 6E, bone anchor 601 includes, in this embodiment, four components: bone screw 620, deflectable post 640, centering rod 660, and cap 610. Centering rod 660 is a cannulated cylindrical rod having a metal tube 690 covered with a tubular polymer sleeve 663. A lumen 692 passes through the full length of metal tube 690. The lumen 692 has a diameter sufficient to pass a guidewire. In a preferred embodiment tube 690 is made of a superelastic metal—for example Nitinol. In one embodiment, tube 690 is a superelastic nitinol wire having a diameter between 0.060 and 0.080 inches. In an exemplary embodiment, tube 690 is a superelastic nitinol wire having a diameter of 0.063 inches. In a preferred embodiment sleeve 663 is made of a wear-resistant biocompatible polymer—for example PEEK.

The proximal end 662 of centering rod 660 is sized and configured to be received within deflectable post 640. The distal end 664 of centering rod 660 is sized and configured to be received within bone screw 620. In a preferred embodiment both ends of centering rod 660 are cylindrical in shape. However, in alternative embodiments, the proximal end 662 and distal end 664 of rod 660 may have other than a circular section, for example, square, oval, rectangular, or other polygonal. Note that the distal end 664 and proximal end 662 of centering rod 660 can have the same, or different, sectional shapes.

The center section 666 of centering rod 660 is designed to bend in response to deflection of deflectable post 640 relative to bone screw 620 and exert a restorative centering force upon deflectable post 640. The restorative force tends to align the longitudinal axis of the deflectable post 640 with the longitudinal axis of the bone screw 620. The force increases as the angle between the deflectable post 640 and bone screw 620 increases. The diameter and shape of center section 666 of centering rod 660 can be designed/selected to achieve a desired restorative force for a given angle and/or direction of deflection. Also, the diameter of tube 690 and thickness of sleeve 663 can be selected to achieve a desired restorative force. Center section 666 can be cylindrical but may have other than a circular section, for example, square, oval, rectangular, or other polygonal. The force/deflection response can accordingly be isotropic or anisotropic depending upon the shape of center section 666.

A hemispherical pocket 639 (shown by dashed lines) is formed in the bottom of cavity 632 of housing 630. A bore 634 (shown by dashed lines) extends distally from the bottom of hemispherical pocket 639 along the longitudinal axis of bone screw 620. Bore 634 is sized and configured to receive the distal end 664 of centering rod 660. Bore 634 is chamfered where it meets hemispherical pocket 639 to allow for bending of centering rod 660. In a preferred embodiment both centering rod 660 and bore 634 are cylindrical in shape such that the distal end 664 of centering rod 660 may rotate about its longitudinal axis within bore 634. Extending and communicating with bore 634 is a further bore 695. Bore 695 extends the full length of the bone screw 620 and communicates with the tip of the bone screw 620 (see FIG. 6E) and thus communicates with the bone that bone screw 620 is adapted to be inserted into. Accordingly, bone screw 620 is a cannulated bone screw. As can be seen in FIG. 6E, bore 695 preferably has a diameter that is smaller than the diameter of bore 634 so as to hold centering rod 660 in bore 634 and not allow centering rod 660 to move into bore 695. The diameter of bore 695 is however preferably sufficient to pass a needle or guidewire or allow the injection or material through the bore.

Deflectable post 640 can be made, for example, from cobalt chrome or titanium. In a preferred embodiment deflectable post 640 is between 4.5 and 6.5 mm in diameter and made in one piece from cobalt chrome. Deflectable post 640 has a retainer 642 at the distal end. Retainer 642 is a ball-shaped or spherical structure in order to form part of a linkage connecting deflectable post 640 to bone screw 620. At the proximal end of deflectable post 640 is a mount 644. Mount 644 is a low profile mount configured to connect deflectable post 640 to a vertical rod component (not shown, but see, e.g. FIGS. 5A-5C). Mount 644 comprises a threaded section 646 to which the vertical rod component may be secured. Mount 644 has at the proximal end a socket 649 which can be engaged by a wrench during the securing of a vertical rod to mount 644.

Extending and communicating with proximal bore 672 is a further bore 693. Bore 693 also communicates with socket 649 so that the deflection post 640 is also cannulated throughout its length. Preferably, the diameter of further bore 693 is less than the diameter of proximal bore 672 so as to contain the centering rod 660 in position between the bone screw 620 and the deflection post 660. The diameter of bore 693 is however preferably sufficient to pass a needle or guidewire or allow the injection or material through the bore.

As shown in FIG. 6E, after assembly, bore 693, bore 695 and lumen 692 are aligned to form a continuous channel which passes through the entire length of bone anchor 601. Furthermore a guidewire, or needle can be inserted through the continuous channel (made up of bore 693, bore 695 and lumen 692) which passes through the entire length of bone anchor 601 in order to guide insertion of the bone anchor.

Accordingly, the above embodiment of the invention includes a cannulated bone anchor such that a cannula is defined by the bone anchor through the deflection post 640, through the centering rod 660 and through the bone screw 620 such that a needle can be inserted through the bone anchor to delivery a medication, a bone cement and/or monitor the bone that the bone anchor is inserted into.

Additionally, a cannulated bone anchor can be introduced into a patient over a guidewire. Once a guidewire is inserted to a desired location, the cannulated bone anchor can be introduced over the guidewire to the desired location. Use of guidewires is particularly useful during percutaneous introduction of bone anchors where the target location of the bone anchor cannot be directly visualized. The guidewire can be, for example a k-wire or other guidewire used in orthopedic surgery to facilitate the positioning of bone anchors. Further, the cannulated bone anchor can provide a port or tube for the ingrowth of bone. Further, the cannulated bone anchor can have a plurality of openings in the bone screw that can preferably communicate with the central bores for enhanced bone ingrowth.

It is to be appreciated that a cannulated bone anchor can include another of the embodiments disclosed herein that do not contain the centering rod 660. By way of example only, the embodiment of the invention in FIGS. 4A-4C can be cannulated with the use of a longitudinal bore through the deflection post 440 and a longitudinal bore through the bone screw 420. Where the bore of the deflection post 440 communicates with the bore of the bone screw 420, the bores can be fluted or broadened out so that they communicate even when the deflection post and the bone screw are not in alignment.

Figure 7A:
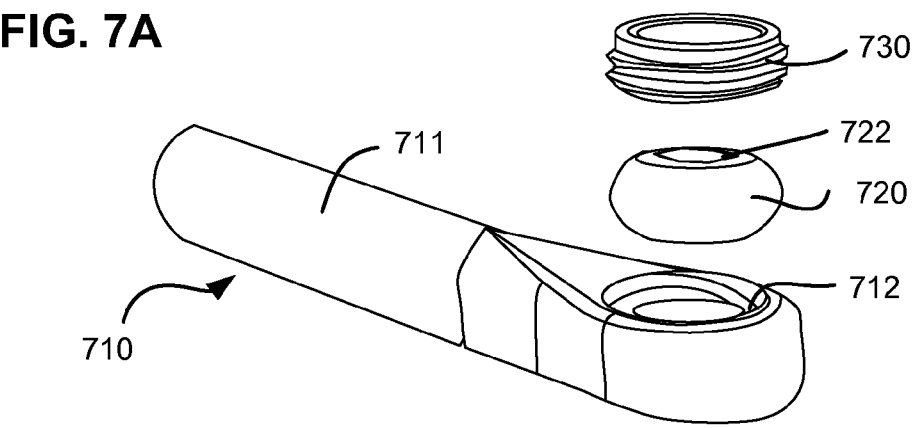
FIG. 7A shows an exploded view of a compound spinal rod suitable for use with the rod connectors of FIGS. 1A and 2A according to embodiments of the invention.

FIG. 7A illustrates another embodiment of a spinal/vertical rod 710 which can be used in conjunction with the rod connectors described above. As shown in FIG. 7A, vertical rod 710 comprises a rod 711 which is preferably a 5.5 mm diameter titanium rod. Vertical rod 710 has a pocket 712 at one end sized to receive a ball 720. Ball 720 is preferably a cobalt chrome ball. Ball 720 has a polygonal aperture 722 designed to closely engage the polygonal section 702 of mount 314. Ball 720 is inserted into pocket 712 and secured into place with threaded cap 730. Pocket 712 is threaded to receive cap 730. Ball 720 is placed in pocket 712 and then cap 730 is screwed into the threaded portion of pocket 712. Cap 730 is preferably titanium and may be laser welded or otherwise secured to vertical rod 710 after assembly. The components of vertical rod 710—titanium rod 711, titanium cap 730 and cobalt chrome ball 720 are assembled prior to use.

Figure 7B:
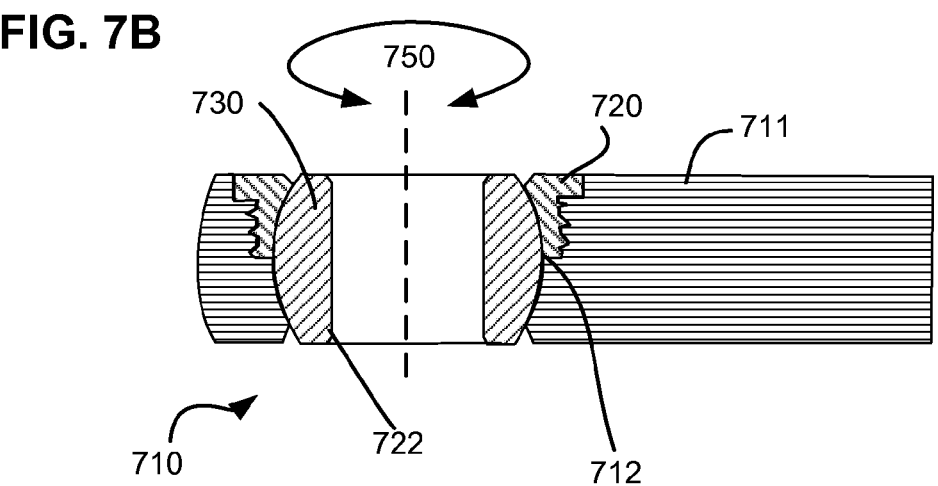
FIG. 7B shows a perspective view of the compound spinal rod of FIG. 7A as assembled.
Figure 7C:
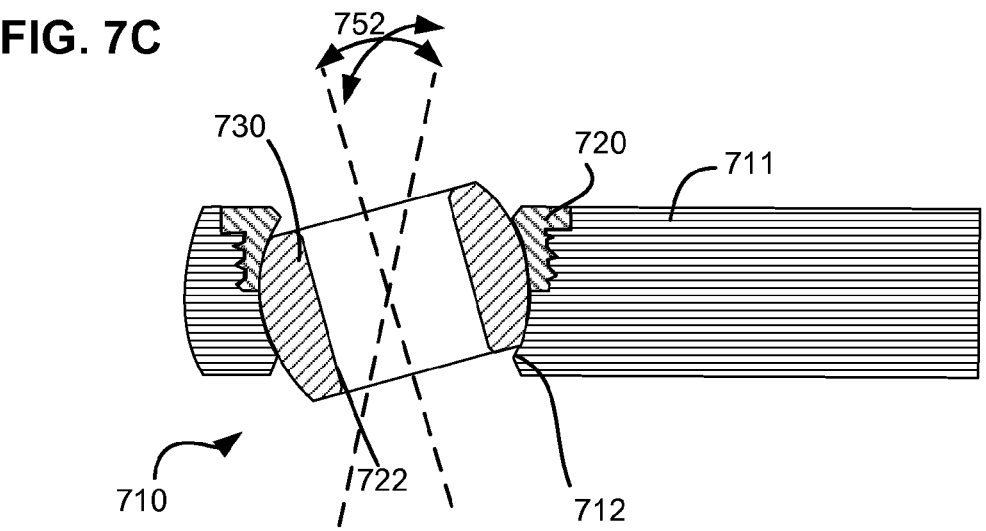
FIG. 7C shows a sectional view of the compound spinal rod of FIG. 7A as assembled.

FIGS. 7B and 7C shows a sectional view through vertical rod 710. FIG. 7B shows ball 720 positioned within pocket 712 of rod 711. As shown in FIG. 7B cap 730 and pocket 712 capture ball 730 such that it cannot be removed from vertical rod 710. Ball 730 can, however, rotate 360 degrees around the axis of aperture 722 as shown by arrow 750. This allows vertical rod 710 to rotate 360 degrees around the long axis of the deflection rod or bone anchor to which ball 730 is mounted. Ball 730 can also tilt from the position shown in FIG. 7B as shown in FIG. 7C by arrows 752. In a preferred embodiment ball 730 can tilt 7 degrees in any direction therefore allowing vertical rod 710 to tilt 7 degrees from perpendicular relative to the deflection rod or bone anchor to which ball 730 is mounted. Note that the mount 314 and a nut to secure the vertical rod 710 to mount 314 are designed so not as to interfere with the range of motion either in rotation or tilting. Vertical rod 710 may be used with a standard bone anchor, or a deflection rod and bone anchor (for example bone anchor 400 of FIGS. 4A-4D), or a polyaxial screw. Likewise, the bone anchor 400 may be utilized with vertical rod 710, but may also be utilized in conjunction with a vertical rod not having a ball joint.

Centering Rods

As illustrated in FIGS. 6A to 6C, embodiments of the bone anchor can include a centering rod in the form of a cylinder of a superelastic metal—for example Nitinol. However, centering rods can be manufactured in a range of different configurations and materials depending upon the desired force deflection characteristics desired for the ball-joint in which they are used. For example, in some embodiments, by adjusting the properties of the centering rod, the deflection characteristics of a bone anchor can be configured to approach the natural dynamic motion of the spine, while giving dynamic support to the spine in that region. It is contemplated, for example, that the flexible bone anchor can replicate a 70% range of motion and flexibility of the natural intact spine, a 50% range of motion and flexibility of the natural intact spine and a 30% range of motion and flexibility of the natural intact spine. In some cases, a kit is provided to a doctor having a set of flexible bone anchors with different force/deflection characteristics from which the doctor may select the flexible bone anchors most suitable for a particular patient. In other cases, the surgeon may select bone anchors prior to the procedure based upon pre-operative assessment. In embodiments centering rod is designed to maintain a deflectable post coaxial with the bone anchor during implantation of the bone anchor thereby ensuring that a desirable range of motion/load sharing is provided.

The stiffness of the centering rod may thus be varied or customized according to the needs of a patient or application. Furthermore, one feature of the present invention is to allow the efficient manufacture of a range of deflectable bone anchors having a range of different force-deflection characteristics. This can readily be accomplished by manufacturing a range of centering rods having different force-deflection characteristics and leaving the remainder of the components unchanged. In this way, the range of deflectable bone anchors is adapted to be manufactured with a minimum number of unique parts.

Alternative designs for centering rods can be utilized in any of the self-centering ball-joints described herein. In some embodiments, the centering rods are provided with a wear-resistant coating and/or sheath on surfaces subject to moving contact in order to reduce wear. Alternatively, the centering rods can be manufactured in whole of in part from materials resistant to wear—for example cobalt chrome. Alternatively, the centering rods are not provided with a wear resistant coating. In preferred embodiments both ends of the centering rod are cylindrical in shape. However, in alternative embodiments, the ends of centering rod 1100a may have other than a circular section, for example, square, oval, rectangular, or other polygonal to match the bore of the housing and ball-rod. Note that the first end and second end of a centering rod can have the same, or different, sectional shapes. Moreover the first end and second end of the centering rod can be sized to be tightly press fit into the bore of the housing and ball-rod to further stabilize the housing relative to the ball-rod. The centering rod can be provided with an enhanced flexibility section between the first end and the second end. The enhanced flexibility section can be provided by: changing/reducing the dimensions of the material in the enhanced flexibility section; changing the material in the enhanced flexibility section; providing grooves/spiral grooves in the enhanced flexibility section, The magnitude of the centering force can be selected based on the design of enhanced flexibility section and the choice of material for the enhanced flexibility section. The centering rod may have the same force deflection response in each direction of deflection of the centering rod (isotropic). The centering rod may alternatively have different force/deflection properties in different directions (anisotropic).

Accordingly, the devices of the present invention provide in some embodiments the ability to control stiffness for extension, flexion, lateral bending and axial rotation, and to control stiffness for each of these motions independently of the other motions. The characteristics of the deflectable post can be changed, for example, by adjusting the diameter of post and/or the properties of the centering rod and/or the distance between the deflectable post and the limit surface. These deflection characteristics need not be isotropic. A bias can be introduced in the deflectable post by varying the shape of the bore, the shape of the centering rod and the space between the deflectable post and the limit surface.

For example, by varying the shape of the cap/socket the distance between the deflectable post and the limit surface may also be varied. By making the distance shorter, the amount of deflection can be reduced that occurs before the increase in stiffness caused by contact with the limit surface. The cap/socket may be shaped to reduce the gap between the post and the limit surface uniformly or may be shaped to reduce the gap between the post and the limit surface more in some directions than in others (anisotropically).

In embodiments where the deflectable post has anisotropic force-deflection response, it is important to ensure that the deflectable post is implanted in the correct orientation. The deflectable post is therefore provided with discernable visual or physical characteristics (e.g. an arrow, color, indentation or other observable indicator) which guide the surgeon to the correct orientation of implantation. When correctly installed, a deflectable post with anisotropic force-deflection response may be used to control stiffness for extension, flexion, lateral bending and axial rotation independently. For example, if a deflectable post is more flexible in the upward direction (relative to the spine after implantation—the head direction being up), the post can deflect more when the spine is placed in flexion and can deflect less when the spine is placed in extension. In effect, this arrangement is more restrictive with respect to movement of the spine with the spine in extension and less restrictive with respect to the movement of the spine with the spine in flexion. Conversely, if the deflectable post is more compliant in the down direction (relative to the spine after implantation—the head direction being up), the post can deflect more when the spine is placed in extension and can deflect less when the spine is placed in flexion. In effect, this arrangement is more restrictive with respect to movement of the spine in flexion and less restrictive with respect to the movement of the spine in extension.

In some embodiments it is desirable for the centering rod to have a sheath made of a material selected to reduced wear caused by moving contact between the centering rod and the deflectable post and/or bone anchor. Thus, for example, the centering rod is, in some embodiments, provided with a sheath made from a wear resistant biocompatible polymer. In a preferred embodiment the sheath 1107g is made from PEEK, however, other biocompatible wear resistant polymers can be used in alternative embodiments. A sheath can be added to any of the centering rods described herein in order to decrease wear at the interface between the centering rod and the ball-rod/deflectable post and/or modulate the force deflection response of the centering rod.

Materials

Movement of the deflectable post relative to the bone anchor provides load sharing and dynamic stabilization properties to the dynamic stabilization assembly. As described above, deflection of the deflectable post deforms the material of the sleeve. In some embodiments, the characteristics of the material of the sleeve in combination with the dimensions of the components of the deflection rod assembly affect the force-deflection curve of the deflection rod. In other embodiments, the characteristics of the material of the centering rod in combination with the dimensions of the components of the assembly affect the force-deflection curve of the assembly.

The rod connector, deflectable post, bone anchor, compound rods, centering rods, and spinal rods are preferably made of biocompatible implantable metals. The rod connector and deflectable post can, for example, be made of titanium, titanium alloy, cobalt chrome alloy, a shape memory metal, for example, Nitinol (NiTi) or stainless steel. In preferred embodiments, the deflectable post is made of cobalt chrome alloy. In preferred embodiments, the rod connector, bone anchor and spinal rods are made of titanium or titanium alloy; however, other materials, for example, stainless steel may be used instead of or in addition to the titanium\titanium alloy components. In a preferred embodiment, the rod connector is machined, in one piece from titanium\titanium alloy. Furthermore, the ball of the dynamic spinal rod is preferably made of cobalt chrome for good wear characteristics.

The material of the sleeve/compliant member/o-ring (where present) is a biocompatible and implantable polymer having the desired deformation characteristics. The material of the sleeve should also be able to maintain the desired deformation characteristics. Thus the material of the sleeve is preferably durable, resistant to oxidation and dimensionally stable under the conditions found in the human body. The sleeve may, for example be made from a polycarbonate urethane (PCU) such as Bionate®. If the sleeve is comprised of Bionate®, a polycarbonate urethane or other hydrophilic polymer, the sleeve can also act as a fluid-lubricated bearing for rotation of the deflectable post relative to the longitudinal axis of the deflectable post.

The material of the sheath of the centering rod (where present) is a biocompatible and implantable polymer having the desired deformation characteristics. The material of the sheath should also be able to maintain the desired deformation characteristics. Thus the material of the sheath is preferably durable, resistant to oxidation and dimensionally stable under the conditions found in the human body. Suitable material includes by way of example only polyetheretherketone (PEEK), polyetherketoneketone (PEKK), polyetherketone (PEK), polyetherketoneetherketoneketone (PEKEKK), and polyetheretherketoneketone (PEEKK). Still, more specifically, the material can be PEEK 450G, which is an unfilled PEEK approved for medical implantation available from Victrex of Lancashire, Great Britain. (Victrex is located at www.matweb.com or see Boedeker www.boedeker.com). Other sources of this material include Gharda located in Panoli, India (www.ghardapolymers.com). As will be appreciated by those of skill in the art, other suitable similarly biocompatible thermoplastic or thermoplastic polycondensate materials that resist fatigue, have good memory, are flexible, and/or deflectable have very low moisture absorption, and good wear and/or abrasion resistance, can be used without departing from the scope of the invention. Reference to other appropriate polymers that can be used in the sheath can be found in the following documents: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and PCT Publication WO 02/00270 A1, dated Jan. 3, 2002, entitled "Bio-Compatible Polymeric Materials." The sheath for the centering rod may also be made, for example, from a polycarbonate urethane (PCU) such as Bionate®.

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated.

The particular dynamic stabilization assemblies shown herein are provided by way of example only. It is an aspect of preferred embodiments of the present invention that a range of components be provided and that the components may be assembled in different combinations and organizations to create different assemblies suitable for the functional needs and anatomy of different patients. Also, bone anchors and deflection rods having different force deflection characteristics may be incorporated at different spinal levels in accordance with the anatomical and functional requirements. Spinal stabilization may be provided at one or more motion segments and in some cases dynamic stabilization may be provided at one or more motion segments in conjunction with fusion at an adjacent motion segment.

Particular embodiments of stabilization assemblies may incorporate combinations of the bone anchors, spinal rods, deflection rods, deflectable posts, centering rods, compound rods, offset and coaxial connectors described herein, and in the related applications incorporated by reference, and standard spinal stabilization and/or fusion components, for example screws, pedicle screws, polyaxial screws and rods. Additionally, any of the implantation tools and methods described herein, and in the related applications incorporated by reference can be used or modified for use with such stabilization assemblies. It is intended that the scope of the invention be defined by the claims and their equivalents.

What is claimed is:

1. A spinal rod connector adapted to connect two spinal rods, the spinal rod comprising:
   a U-shaped housing with first and second arms with first and second elongated lengths respectively, which first and second elongated lengths are about parallel to each other;
   said housing including a first channel that defines a spherical socket and a second channel that is cylindrical and includes a gap where the first arm is spaced from the second arm;
   a rod mount with a bore positioned in said first channel, which rod mount can move relative to the first channel, and said rod mount is a compression ball with a slot;
   a fastener provided through the housing between the first channel and the second channel and wherein the gap is located distally from said fastener and the fastener does not come in contact with the gap, whereby the first channel and rod mount are adapted to capture a first spinal rod provided through the bore of said rod mount, and said second channel is adapted capture a second spinal rod when the fastener is actuated to bring together said first arm and said second arm and thereby closing the gap and with the first rod being one of parallel and non-parallel to the second rod.

2. The spinal rod connector of claim 1 wherein said rod mount is spherical.

3. The spinal rod connector of claim 1 wherein said rod mount includes at least one said slot that is adapted to allow said rod connector to capture a spinal rod in said rod mount when said fastener is actuated.

4. The spinal rod connector of claim 1 wherein said first channel and said rod mount form a ball joint.

5. The spinal rod connector of claim 1 wherein said rod mount includes at least one lip that limits the motion of said rod mount in said first channel.

6. The spinal rod connector of claim 1 wherein said rod mount is spherical and includes slots.

7. The spinal rod connector of claim 1 wherein said rod mount is free to rotate and pivot inside of said first channel prior to the use of the fastener which is adapted to capture the spinal rod in said bore of said rod mount.

8. The spinal rod connector of claim 1 wherein said fastener is a bolt with one of a hex head and a hex socket.

9. The spinal rod connector of claim 1 in combination with first and second spinal rod, wherein said first and second spinal rods can be captured in said spinal rod connector with the first and second spinal rods being one of parallel to each other and non-parallel to each other.

* * * * *